United States Patent [19]

Tabe et al.

[11] Patent Number: 5,604,257
[45] Date of Patent: Feb. 18, 1997

[54] LACTONE COMPOUND AND PROCESS OF PRODUCTION THEREOF

[75] Inventors: Masayasu Tabe; Kenji Manabe, both of Hino; Koji Tomimori, Hachioji; Atsuo Hazato, Hino; Osami Takenouchi, Hino; Yoshiaki Azuma, Hino, all of Japan

[73] Assignee: Teijin Limited, Osaka, Japan

[21] Appl. No.: 191,593

[22] Filed: Feb. 4, 1994

[30] Foreign Application Priority Data

Feb. 5, 1993 [JP] Japan .................................. 5-18703
Mar. 26, 1993 [JP] Japan .................................. 5-68434

[51] Int. Cl.$^6$ ............................ A61K 31/35; A61K 31/34
[52] U.S. Cl. ......................... 514/460; 514/473; 549/292; 549/313
[58] Field of Search ...................... 549/292, 313; 514/460, 473

[56] References Cited

U.S. PATENT DOCUMENTS 4,511,564  4/1985  Ishizuka et al. ................. 514/167

FOREIGN PATENT DOCUMENTS 58-118516   7/1983   Japan .
58-210011  12/1983   Japan .
60-185715   9/1985   Japan .
62-175496   8/1987   Japan .

OTHER PUBLICATIONS

The Journal of Organic Chemistry vol. 57, No. 1, 3 Jan. 1992, Washington, U.S. pp. 33–39.
The Journal of Organic Chemistry vol. 48, No. 23, 18 Nov. 1983, Washington, U.S., pp. 4433–4436.
Journal of the Chemical Society, Chemical Communications No. 17, 1 Sep. 1992, Letchworth, GB pp. 1229–1231.

Primary Examiner—C. Warren Ivy
Assistant Examiner—Amelia Owens
Attorney, Agent, or Firm—Sughrue, Mion, Zinn, Macpeak & Seas

[57] ABSTRACT

A lactone compound, useful as an osteogenetic accelerator, having the formula (I):

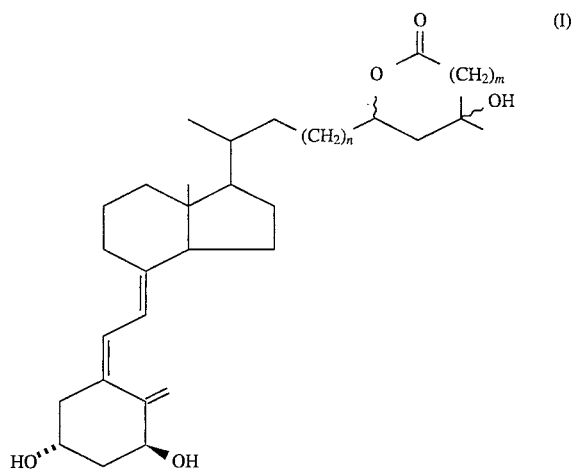

wherein n is zero or 1 and m is zero or 1, provided that both n and m are not zero at the same time, or a stereoisomer thereof at the 23- and/or 25-positions or any mixture thereof and a production process thereof.

10 Claims, No Drawings

LACTONE COMPOUND AND PROCESS OF PRODUCTION THEREOF

BACKGROUND OF THE INVENTION

1. Field of the Invention

The present invention relates to a vitamin $D_3$ based lactone, derivative which is useful as a pharmaceutical. More specifically, it relates to 1α,25-dihydroxy vitamin $D_3$ based lactone derivatives useful as an accelerator of bone formation (i.e., an osteogenetic accelerator), a suppressant of tumor cell proliferation, a drug for treating hypercalcemia, or other pharmaceuticals, a process for production of the same, and an intermediate for the production thereof.

2. Description of the Related Art

The fact that the metabolites of vitamin $D_3$ perform an extremely important function as substances controlling the metabolism of calcium and phosphates in the living body is now becoming widely recognized through numerous disclosures in patents and general references. Recently, further, an increase is being seen in clinical applications as drugs for treatment of various ailments, such as with the discovery of numerous substances having the ability to induce differentiation of tumorous bone marrow cells. Further, recently, a novel vitamin $D_3$ active metabolite having an α-hydroxy-lactone ring at a steroid side chain has been discovered (Arch. Biochem. Biophys., 204, 339–391 (1980); FEBS LETTERS, 134, 207–211 (1981)). This compound is 1α,25-dihydroxy-vitamin $D_3$-26,23-lactone and is represented by the structure shown below:

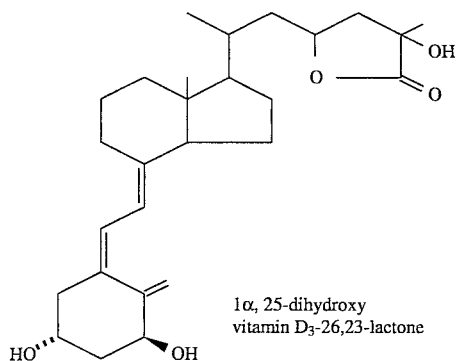

1α, 25-dihydroxy vitamin $D_3$-26,23-lactone

This compound is reported to have actions such as an action of lowering the concentration of calcium in blood serum (Japanese Unexamined Patent Publication (Kokai) No. 58-118516), an action of suppressing the proliferation of tumorous cells (Japanese Unexamined Patent Publication (Kokai) No. 58-210011), an action of accelerating bone formation (Japanese Unexamined Patent Publication (Kokai) No. 60-185715), etc. and is expected to contribute much as a drug for treatment of various ailments.

SUMMARY OF THE INVENTION

Accordingly, the objects of the present invention are to provide a novel lactone compound, and a production process thereof, which is expected to be useful as pharmaceuticals, for example, an accelerator of bone formation, a suppressant of tumor cell proliferation, and a drug for treating hypercalcemia.

Other objects and advantages of the present invention will be apparent from the following description.

In accordance with the present invention, there is provided a lactone compound having the formula (I):

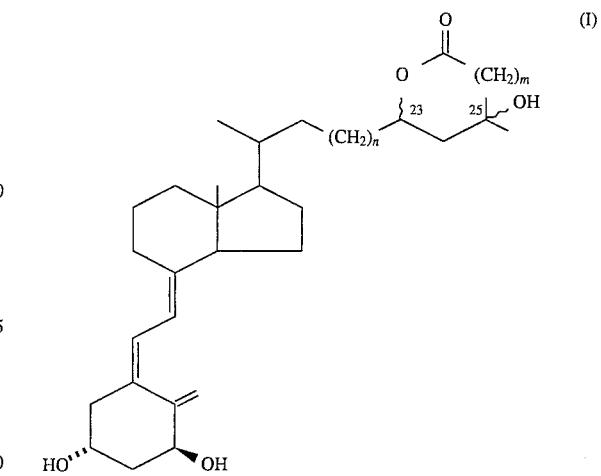

wherein n is zero or 1 and m is zero or 1, provided that both n and m are not zero at the same time, or a stereoisomer thereof at the 23- and/or 25-positions or any mixture thereof.

In accordance with the present invention, there is also provided a 1α,25-dihydroxy-22-homomethylene-vitamin $D_3$-26,23-lactone compound having the formula (II):

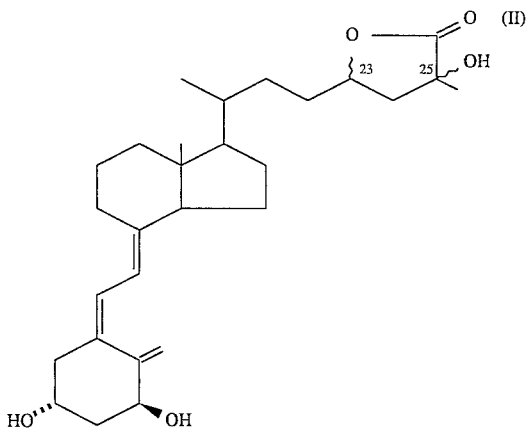

a stereoisomer thereof at 23- and/or 25-positions or any mixture thereof.

In accordance with the present invention, there is also provided the above-mentioned optically active lactone compound, wherein an asymmetric center at C-23 is an (S) configuration and an asymmetric center at C-25 is an (R) configuration, or wherein an asymmetric center at C-23 is an (R) configuration and an asymmetric center at C-25 is an (R) configuration.

In accordance with the present invention, there is further provided a process for producing a lactone compound having the above-mentioned formula (I) or a stereoisomer thereof at the 23- and/or 25-positions or any mixture thereof, or a 1α,25-dihydroxy-22-homomethylene-vitamin $D_3$-26, 23-lactone having an asymmetric center at C-23 of an (R) configuration and an asymmetric center at C-25 of an (R) configuration or having an asymmetric center at C-23 of an (R) configuration and an asymmetric center at C-25 of an (R) configuration, or 1α,25-dihydroxy-26-homomethylene-vitamin $D_3$-26,23-lactone comprising:

(i) allowing to subject to a halogenation reaction (a) a lactone compound, which is asteroid compound having the formula (IV):

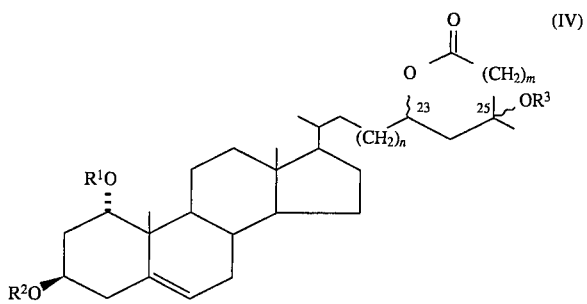

(IV)

wherein n is zero or 1 and m is zero or 1, provided that both n and m are not zero at the same time, $R^1$, $R^2$ and $R^3$ may be the same or different and represent a hydrogen atom, a tri($C_1$–$C_7$ hydrocarbon) silyl group, a $C_2$–$C_7$ acyl group or a group forming an acetal linkage together with an oxygen atom of a hydroxyl group, a stereoisomer thereof at the 23- and/or 25-positions or any mixture thereof, or (b) 1α,25-dihydroxy-22-homomethylene-cholest-5-ene-26,23-lactone, having an asymmetric center at C-23 of an (S) configuration and an asymmetric center at C-25 of an (R) configuration or having an asymmetric center at C-23 of an (R) configuration and an asymmetric center at C-25 of an (R) configuration or (c) 1α,25-dihydroxy-26-homomethylene-cholest-5-ene-26,23-lactone having an asymmetric center at C-23 of an (S) configuration and an asymmetric center at C-25 of an (R) configuration, followed by treating with a basic compound and, when the hydroxyl group is protected with a protecting group, removing the protecting group from the hydroxyl group, to thereby obtain (a) a lactone compound, which is a steroid compound having the formula (V):

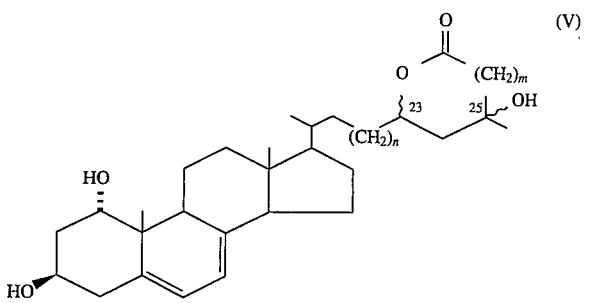

(V)

wherein n is zero or 1 and m is zero or 1, provided that both n and m are not zero at the same time, a stereoisomer thereof at 23- and/or 25-positions or any mixture thereof or (b) 1α,25-dihydroxy-22-homomethylene-cholesta-5,7-diene-26,23-lactone having an asymmetric center at C-23 of an (S) configuration and an asymmetric center at C-25 of an (R) configuration or having an asymmetric center at C-23 of an (R) configuration and an asymmetric center at C-25 of an (R) configuration or 1α,25-dihydroxy-26-homomethylene-cholesta-5,7-diene-26,23-lactone, and (ii) subjecting the same to a photo-isomerization reaction.

In accordance with the present invention, there is still further provided a lactone compound, which is a steroid compound having the formula (VI):

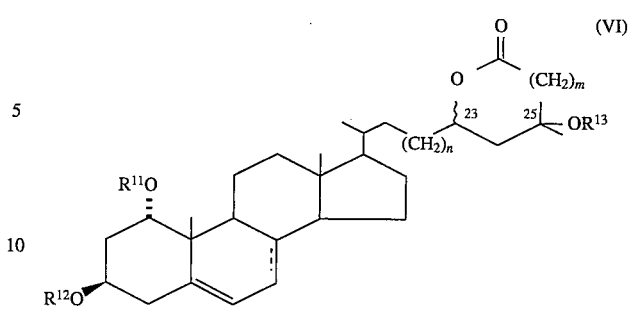

(VI)

wherein n is zero or 1 and m is zero or 1, provided that both n and m are not zero at the same time, $R^{11}$, $R^{12}$ and $R^{13}$ are the same or different and represent a hydrogen atom, a tri($C_1$–$C_7$ hydrocarbon) silyl group, a $C_2$–$C_7$ acyl group or a group forming an acetal linkage together with an oxygen atom of a hydroxyl group, the symbol "$\text{-}\text{-}$" is a single bond or a double bond, a stereoisomer thereof at the 23- and/or 25-positions or any mixture thereof.

In accordance with the present invention, there is still further provided an osteogenetic accelerator containing, as an active agent, the compound having the above-mentioned formula (I).

DESCRIPTION OF THE PREFERRED EMBODIMENTS

Specific examples of the preferable vitamin-$D_3$ lactone compounds of the present invention having the above-mentioned formula (I) are as follows:

1) 1α,25-dihydroxy-22-homomethylene-vitamin $D_3$-26,23-lactone
2) 23(S),25(R)-1α,25-dihydroxy-22-homomethylene-vitamin $D_3$-26,23-lactone
3) 23(R),25(S)-1α,25-dihydroxy-22-homomethylene-vitamin $D_3$-26,23-lactone
4) 23(S),25(S)-1α,25-dihydroxy-22-homomethylene-vitamin $D_3$-26,23-lactone
5) 23(R),25(R)-1α,25-dihydroxy-22-homomethylene-vitamin $D_3$-26,23-lactone
6) 1α,25-dihydroxy-26-homomethylene-vitamin $D_3$-26,23-lactone
7) 23(S),25(R)-1α,25-dihydroxy-26-homomethylene-vitamin $D_3$-26,23-lactone
8) 23(R),25(S)-1α,25-dihydroxy-26-homomethylene-vitamin $D_3$-26,23-lactone
9) 23(S),25(S)-1α,25-dihydroxy-26-homomethylene-vitamin $D_3$-26,23-lactone
10) 23(R),25(R)-1α,25-dihydroxy-26-homomethylene-vitamin $D_3$-26,23-lactone
11) 1α,25-dihydroxy-22,26-dihomomethylene-vitamin $D_3$-26,23-lactone
12) 23(S),25(R)-1α,25-dihydroxy-22,26-dihomomethylene-vitamin $D_3$-26,23-lactone
13) 23(R),25(S)-1α,25-dihydroxy-22,26-dihomomethylene-vitamin $D_3$-26,23-lactone
14) 23(S),25(S)-1α,25-dihydroxy-22,26-dihomomethylene-vitamin $D_3$-26,23-lactone
15) 23(R),25(R)-1α,25-dihydroxy-22,26-dihomomethylene-vitamin $D_3$-26,23-lactone The above-mentioned lactone compounds are expected to be useful as pharmaceuticals, for example, an accelerator of bone formation, a suppressant of tumor cell proliferation, and a drug for treating hypercalcemia.

As set forth above, the lactone compound (I) according to the present invention can be prepared from the above-mentioned compound (IV) through the above-mentioned compound (V), as shown in the following reaction schemes.

The compound (IV) can be prepared from the method as disclosed in Japanese Unexamined Patent Publication (Kokai) No. 62-175496, as shown in the following schemes.

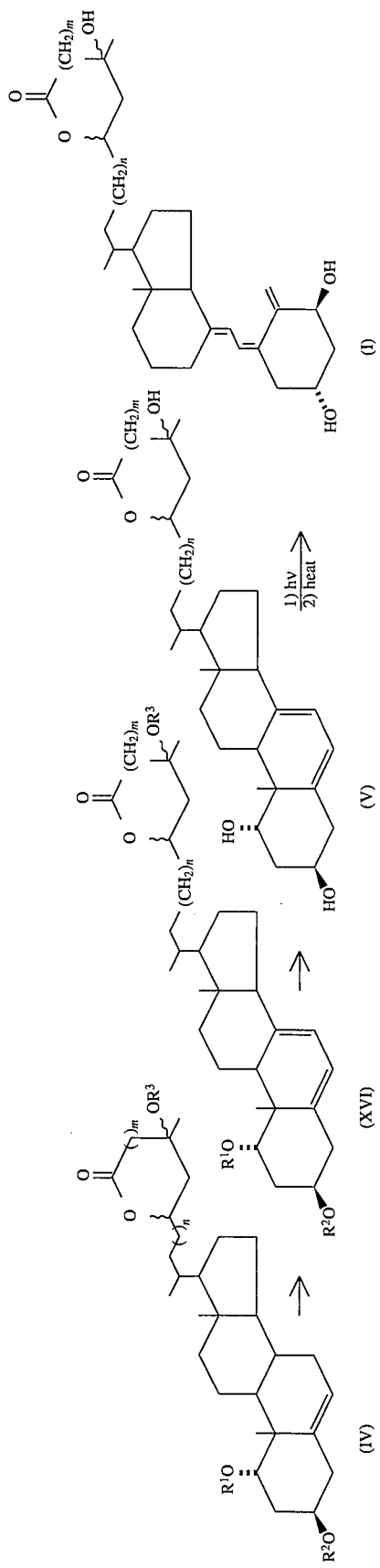
(n = 1, m = 0)   or   (n = 1, m = 1)   or   (n = 0, m = 1)

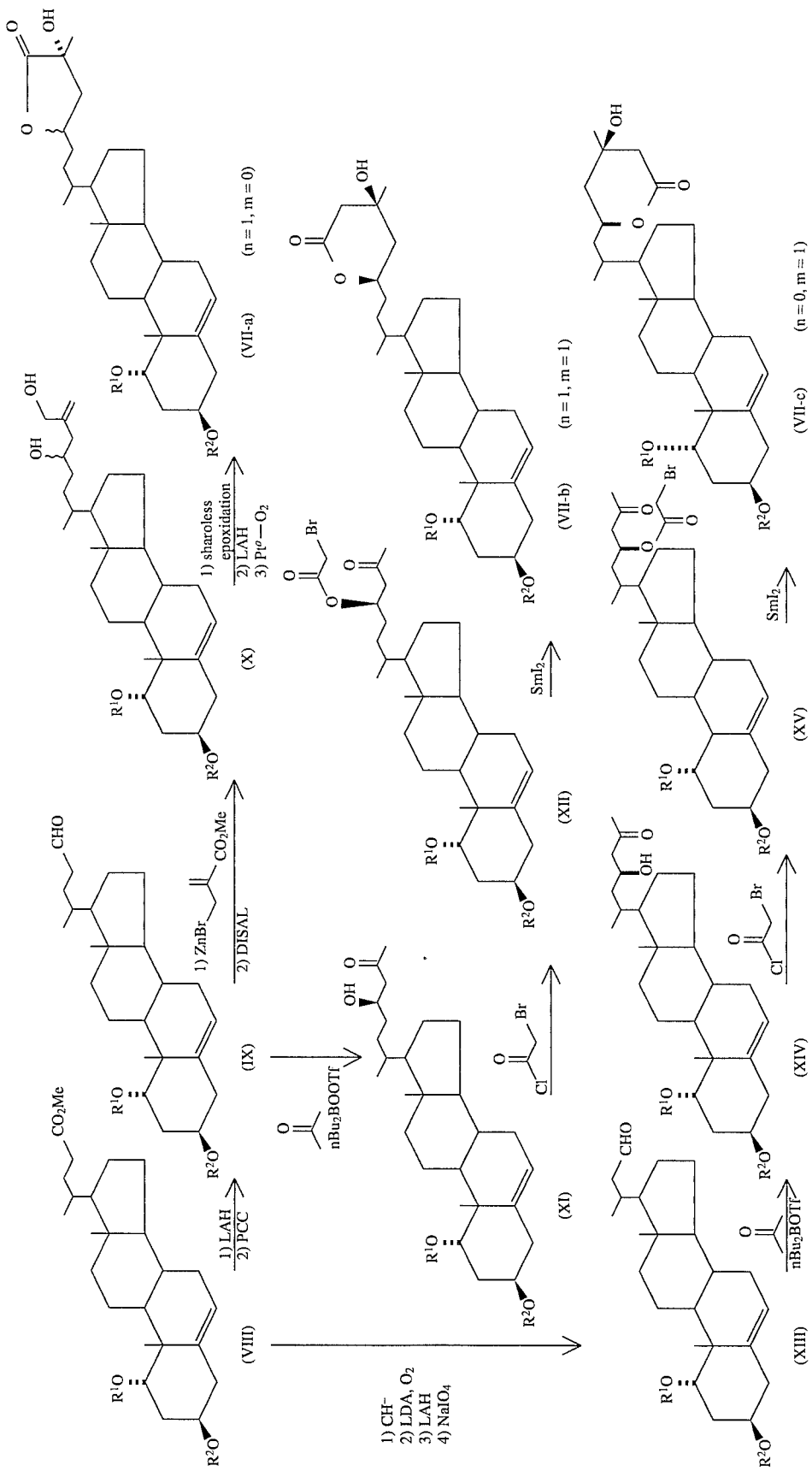

According to the present invention, as the preferable compounds, provided are the 1α,25-dihydroxy-22-homomethylene-vitamin $D_3$-26,23-lactones having the above-mentioned formula (II) the stereoisomers thereof at the 23- and/or 25-positions or any mixtures thereof, especially 23(S),25(R)-1α,25-dihydroxy-22-homomethylene-vitamin $D_3$-26,23-lactone compounds which are compounds having an asymmetric center at C-23 of an (S) configuration and an asymmetric center at C-25 of an (R) configuration.

Further, in formula (I), the wavy line ～ represents """ or ▬. The wavy lines in the same compound may have the same or different meaning, but preferably the wavy line of the 23-position is """ and the wavy line ～ of the 25-position is """ or the wavy line ～ of the 23-position is ▬ and the wavy line ～ of the 25-position is """.

The lactone compounds are expected to be useful as pharmaceuticals, for example a promoter of bone formation, a suppressant of tumor cell proliferation, and a drug for treating hypercalcemia.

The 1α,25-dihydroxy-22-homomethylene-vitamin $D_3$-26,23-lactone compounds of the formula (II) of the present invention are realized by subjecting to a halogenation reaction 1α,25-dihydroxy-22-homomethylene-cholest-5-ene-26,23-lactone compounds, which are steroid compounds of the following formula (IV-a).

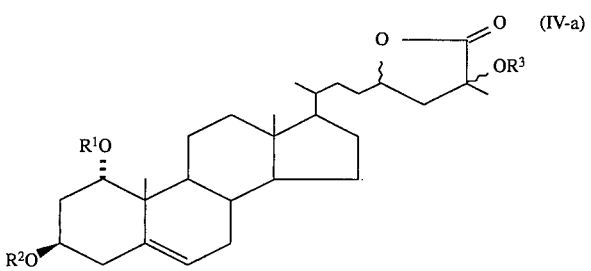

(IV-a)

wherein, $R^1$, $R^2$, and $R^3$ are the same or different and are a hydrogen atom, tri($C_1$–$C_7$ hydrocarbon) silyl group, a $C_2$–$C_7$ acyl group, or a group forming an acetal bond together with an oxygen atom of a hydroxyl group, stereoisomers relating to their 23-position and/or 25-position, or any mixtures of the same, particularly preferably 23(S), 25(R)-1α,25-dihydroxy-22-homomethylene-cholest-5-ene-26,23-lactone compounds or 23(R),25(R)-1α,25-dihydroxy-22-homomethylene-cholest-5-ene-26,23-lactone compounds, then treating them by a basic compound and, when there is a protective group of the hydroxyl group, subjecting them to a deprotecting reaction, thereby obtaining 1α,25-dihydroxy-22-homomethylene-cholesta-5,7-diene-26,23-lactone compounds, which are steroid compounds of the following formula (V-a):

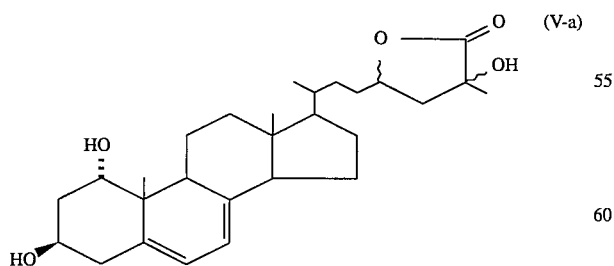

(V-a)

stereoisomers relating to their 23-position and/or 25-position, or mixtures of any proportions of the same, particularly preferably 23(S),25(R)-1α,25-dihydroxy-22-homomethylene-cholesta-5,7-diene-26,23-lactone compounds or 23(R), 25(R)-1α,25-dihydroxy-22-homomethylene-cholesta5,7-diene-26,23-lactone compounds, then subjecting them to a photoreaction and isomerization.

The compounds represented by the above formula (IV-a) of the present invention can be synthesized in accordance with the following precise scheme from the compound of the formula (VIII) as stated above. The method of synthesis of the starting substance compound of the formula (VIII) is disclosed in Japanese Unexamined Patent Publication (Kokai) No. 62-175496.

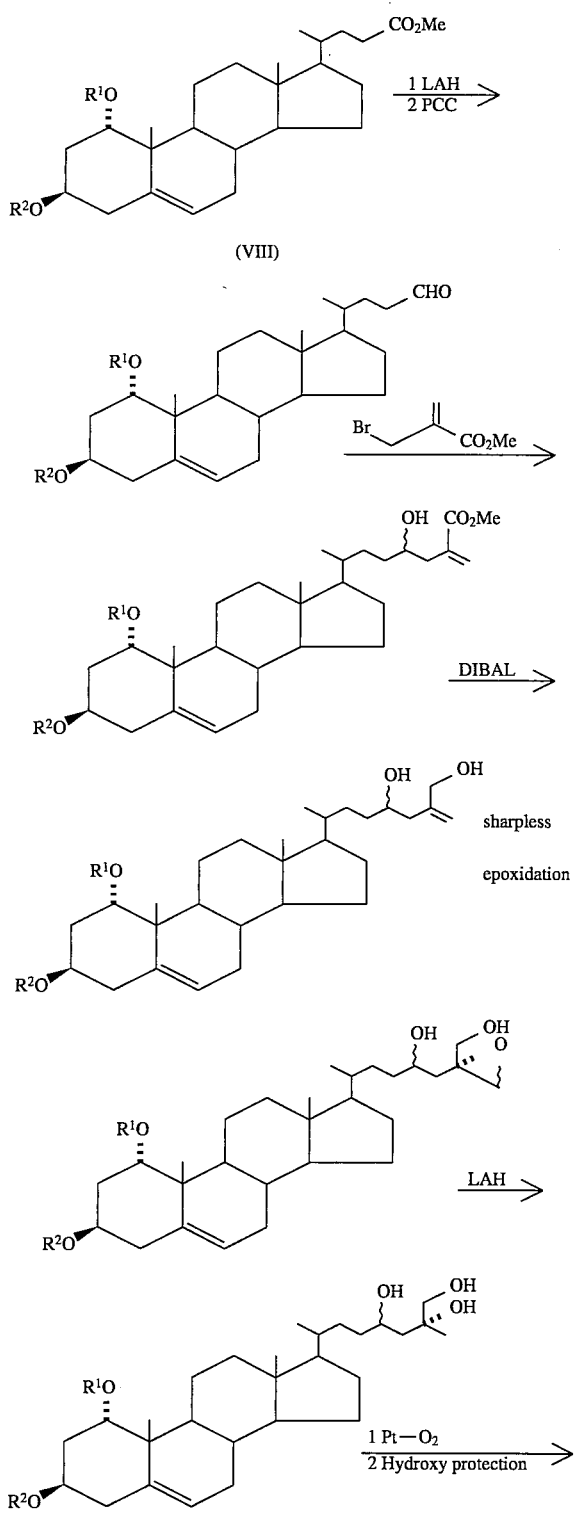

13
-continued

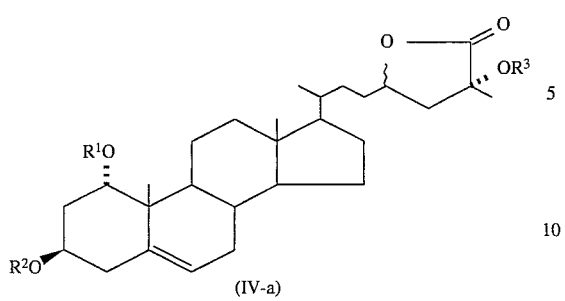
(IV-a)

In the above-mentioned scheme, $R^1$ and $R^2$ are the same or different and are a hydrogen atom, tri($C_1$–$C_7$ hydrocarbon) silyl group, a $C_2$–$C_7$ acyl group, or a group forming an acetal bond together with an oxygen atom of a hydroxyl group.

Further, according to the present invention, it is possible to synthesize the compound (V-a) by the following steps:

(Step 1)

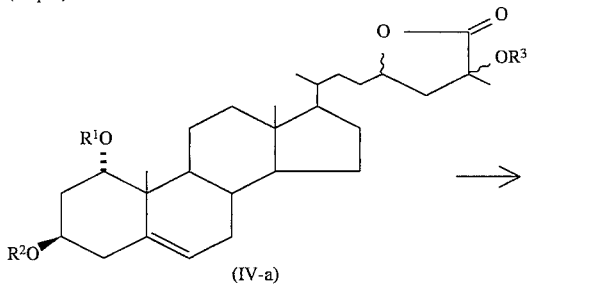
(IV-a)

↓

(XVI-a)

(Step 2)

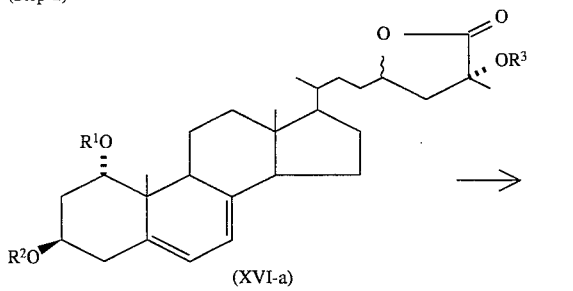
(XVI-a)

→

14
-continued

(V-a)

(Step 3)

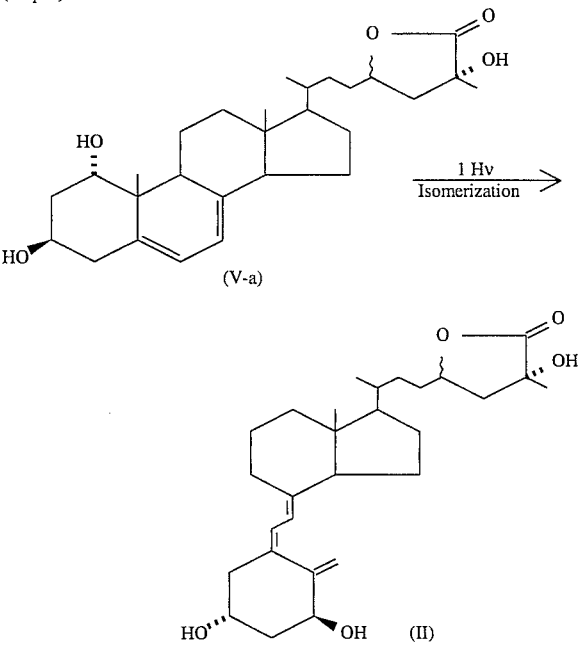

In the above scheme, $R^1$, $R^2$, and $R^3$ are the same or different and are a hydrogen atom, tri($C_1$–$C_7$ hydrocarbon) silyl group, a $C_2$–$C_7$ acyl group, or a group forming an acetal bond together with an oxygen atom of a hydroxyl group.

In the above formulae (IV-a) and (IV-a), when $R^1$, $R^2$, or $R^3$ represents a tri($C_1$–$C_7$ hydrocarbon) silyl group, as specific examples, mention may be made of the trimethylsilyl, triethylsilyl, and t-butyldimethyl silyl groups and other tri($C_1$–$C_4$ alkyl) silyls; the t-butyldiphenylsilyl group and other diphenyl ($C_1$–$C_4$) alkylsilyls; the tribenzylsilyl group, or dimethyl-(2,4,6-tri-t-butylphenoxy)silyl group, etc. as preferable examples.

In the above formulae (IV) and (IV-a), when $R^1$, $R^2$, or $R^3$ represents a $C_1$–$C_7$ acyl group, as specific examples, mention may be made of acetyl, propionyl, n-butyryl, iso-butyryl, n-valeryl, iso-valeryl, caproyl, enanthyl, benzoyl, methoxycarbonyl, ethoxycarbonyl, benzyloxycarbonyl, etc. Among these, $C_2$–$C_6$ acyl groups, for example, acetyl, n- or iso-butyl, benzoyl, methoxycarbonyl, and ethoxycarbonyl are preferable.

In the above formulae (IV) and (IV-a), when $R^1$, $R^2$, or $R^3$ represents a group forming an acetal bond with the oxygen atom of a hydroxyl group, as specific examples, mention may be made of the methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, 4-(4-methoxytetrahydropyranyl) groups, the 5,6-dimethyl-3-oxa-2bicyclo[3.1.0]hex-4-yl group, etc. Among these, the methoxymethyl, (2-methoxyethoxy)methyl, benzyloxymethyl, and 2-tetrahydropyranyl groups are preferable.

Next, the process of production of the compounds of the above-mentioned formulas (V-a) and (II) of the present invention will be explained.

(Step 1)

The compound (XVI-a) is obtained by causing the compound (IV-a) to undergo a halogenation reaction by an N-bromoimide, then is made to undergo dehydrohalogenation. As the N-bromoimide which can be used in the halogenation reaction, several may be mentioned, but preferably use is made of N-bromosuccinimide and 1,3-dibromo-5,5-dimethyl-hydantoin. The halogenation reaction is performed in a usual organic solvent. For example, use may be made of cyclohexane, n-hexane, carbon tetrachloride, and mixtures of the same, but use may be made of any solvent even other than these solvents so long as they do not have an adverse effect on the reaction. The reaction time and the reaction temperature are not particularly limited, but usually the reaction is performed under heating of 50° to 120° C. and ended in from 10 minutes to 3 hours. In the following dehydrohalogenation reaction, as the reagent for the dehydrohalogenation, several may be mentioned, such as organic amines, but preferably use is made of s-collidine or tetra-n-butylammoniumfluoride. The dehydrohalogenation reaction is performed in a usual organic solvent. For example, use may be made of toluene, xylene, tetrahydrofuran, methylene chloride, or mixtures of the same, but any solvent may be used in addition to these solvents so long as they do not have an adverse effect on the reaction. The reaction time and the reaction temperature are not particularly limited, but usually the reaction is performed under 0° to 160° C. and ended in from 10 minutes to 3 hours.

(Step 2)

The compound (V-a) is obtained by removing the protective groups of the hydroxyl groups of the compound (XVI-a).

When $R^1$, $R^2$, or $R^3$ are silyl groups, it may be obtained by treatment by hydrogen fluoride-pyridine, tetra-n-butylammonium-fluoride, etc. When an acyl group, it may be obtained by sodium hydroxide, potassium hydroxide, lithium hydroxide, and the like in aqueous solution When $R^1$, $R^2$, $R^3$ or is a group forming an acetal bond together with an oxygen atom of a hydroxyl group, it may be obtained by treatment by hydrochloric acid and other acids. When $R^1$, $R^2$, or $R^3$ are different, it may be obtained by a combination of the above methods. The deprotecting reaction is performed in an ordinary organic solvent. For example, use may be made of ethanol, methanol, tetrahydrofuran, acetonitrile, methylene chloride, and the like and mixtures of the same. Any solvent even outside of these solvents may be used as well so long as they have no adverse effect on the reaction. The reaction temperature and the reaction time of the deprotecting reaction are not particularly limited, but the reaction may be performed at 0° to 60° C. and end within 1 to 48 hours.

(Step 3)

In the photoreaction of the compound (V-a) ultraviolet light is irradiated into an organic solvent to cause the reaction.

As the organic solvent, mention may be made of ethanol, ethyl acetate, tetrahydrofuran, etc., but the solvents are not limited to these. As the light source of the ultraviolet light, mention may be made of a high voltage mercury lamp, a laser (254 nm, 300 nm, 350 nm), etc., but the invention is not limited to these. As the isomerization reaction, the compound may be heated at from room temperature to 120° C. and agitated for 1 hour to several days to make it react.

Further, in the present invention, there are provided 1α,25-dihydroxy-22-homomethylene-cholesto-5-ene-26,23-lactones or 1α,25-dihydroxyl-22-homomethylene-cholesta-5,7-diene-26,23-lactones, which are steroid compounds of the following formula (VI-a):

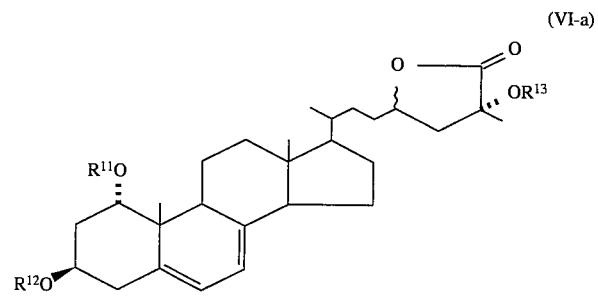

(VI-a)

wherein, $R^{11}$, $R^{12}$, or $R^{13}$ are the same or different and are a hydrogen atom, tri($C_1$–$C_7$ hydrocarbon) silyl group, $C_2$–$C_7$ acyl group, or a group forming an acetal bond together with an oxygen atom of a hydroxyl group and $\underline{\phantom{xx}}$ represents that the bond is a single bond or a double bond), stereoisomers relating to their 23-position and/or 25-position, or mixtures of any proportions of the same. Here, as specific examples of $R^{11}$, $R^{12}$, and $R^{13}$, the same as those described for the above-mentioned $R^1$, $R^2$, and $R^3$ may be illustrated.

As specific examples of the compounds represented by formula (VI-a) of the present invention, mention may be made of the following. Note that these compounds of the formula (VI-a) are useful as intermediates for synthesis of the compounds of formula (II) which are useful as pharmaceuticals.

1) 23(S),25(R)-1α,25-dihydroxy-22-homomethylene-cholest-5-ene-26,23-lactone
2) 23(R),25(R)-1α,25-dihydroxy-22-homomethylene-cholest-5-ene-26,23-lactone
3) 23(S),25(S)-1α,25-dihydroxy-22-homomethylene-cholest-5-ene-26,23-lactone
4) 23(R),25(S)-1α,25-dihydroxy-22-homomethylene-cholest-5-ene-26,23-lactone
5) 23(S),25(R)-1α,25-dihydroxy-22-homomethylene-cholesta-5,7-diene-26,23-lactone
6) 23(R),25(R)-1α,25-dihydroxy-22-homomethylene-cholesta-5,7-diene-26,23-lactone
7) 23(S),25(S)-1α,25-dihydroxy-22-homomethylene-cholesta-5,7-diene-26,23-lactone
8) 23(R),25(S)-1α,25-dihydroxy-22-homomethylene-cholesta-5,7-diene-26,23-lactone
9) 23(S),25(R)-1α,25-dihydroxy-22-homomethylene-cholest-5-ene-26,23-lactone-1,3,25-tris-t-butyldimethylsilylether
10) 23(R),25(R)-1α,25-dihydroxy-22-homomethylene-cholest-5-ene-26,23-lactone-1,3,25-tris-t-butyldimethylsilylether
11) 23(S),25(S)-1α,25-dihydroxy-22-homomethylene-cholest-5-ene-26,23-lactone-1,3,25-tris-t-butyldimethylsilylether
12) 23(R),25(S)-1α,25-dihydroxy-22-homomethylene-cholest-5-ene-26,23-lactone-1,3,25-tris-t-butyldimethylsilylether 13) 23(S),25(R)-1α,25-dihydroxy-22-homomethylene-cholesta-5,7-diene-26,23-lactone-1,3,25-tris-t-butyldimethylsilylether
14) 23(R),25(R)-1α,25-dihydroxy-22-homomethylene-cholesta-5,7-diene-26,23-lactone-1,3,25-tris-t-butyldimethylsilylether
15) 23(S),25(S)-1α,25-dihydroxy-22-homomethylene-cholesta-5,7-diene-26,23-lactone-1,3,25-tris-t-butyldimethylsilylether
16) 23(R),25(S)-1α,25-dihydroxy-22-homomethylene-cholesta-5,7-diene-26,23-lactone-1,3,25-tris-t-butyldimethylsilylether
17) 23(S),25(R)-1α,25-dihydroxy-22-homomethylene-cholest-5-ene-26,23-lactone-1,3,25-tris-methoxymethelether
18) 23(R),25(R)-1α,25-dihydroxy-22-homomethylene-cholest-5-ene-26,23-lactone-1,3,25-tris-methoxymethelether
19) 23(S),25(S)-1α,25-dihydroxy-22-homomethylene-cholest-5-ene-26,23-lactone-1,3,25-tris-methoxymethelether
20) 23(R),25(S)-1α,25-dihydroxy-22-homomethylene-cholest-5-ene-26,23-lactone-1,3,25-tris-methoxymethelether
21) 23(S),25(R)-1α,25-dihydroxy-22-homomethylene-cholesta-5,7-diene-26,23-lactone-1,3,25-tris-methoxymethelether
22) 23(R),25(R)-1α,25-dihydroxy-22-homomethylene-cholesta-5,7-diene-26,23-lactone-1,3,25-tris-methoxymethelether
23) 23(S),25(S)-1α,25-dihydroxy-22-homomethylene-cholesta-5,7-diene-26,23-lactone-1,3,25-tris-methoxymethelether
24) 23(R),25(S)-1α,25-dihydroxy-22-homomethylene-cholesta-5,7-diene-26,23-lactone-1,3,25-tris-methoxymethelether
25) 23(S),25(R)-1α,25-dihydroxy-22-homomethylene-cholest-5-ene-26,23-lactone-1,3,25-tris-acetate
26) 23(R),25(R)-1α,25-dihydroxy-22-homomethylene-cholest-5-ene-26,23-lactone-1,3,25-tris-acetate
27) 23(S),25(S)-1α,25-dihydroxy-22-homomethylene-cholest-5-ene-26,23-lactone-1,3,25-tris-acetate
28) 23(R),25(S)-1α,25-dihydroxy-22-homomethylene-cholest-5-ene-26,23-lactone-1,3,25-tris-acetate
29) 23(S),25(R)-1α,25-dihydroxy-22-homomethylene-cholesta-5,7-diene-26,23-lactone-1,3,25-tris-acetate
30) 23(R),25(R)-1α,25-dihydroxy-22-homomethylene-cholesta-5,7-diene-26,23-lactone-1,3,25-tris-acetate
31) 23(S),25(S)-1α,25-dihydroxy-22-homomethylene-cholesta-5,7-diene-26,23-lactone-1,3,25-tris-acetate
32) 23(R),25(S)-1α,25-dihydroxy-22-homomethylene-cholesta-5,7-diene-26,23-lactone-1,3,25-tris-acetate
33) 23(S),25(R)-1α,25-dihydroxy-22-homomethylene-cholesta-5-ene-26,23-lactone-1,3,25-tris-ethoxycarboxylate
34) 23(R),25(R)-1α,25-dihydroxy-22-homomethylene-cholest-5-ene-26,23-lactone-1,3,25-tris-ethoxycarboxylate
35) 23(S),25(S)-1α,25-dihydroxy-22-homomethylene-cholest-5-ene-26,23-lactone-1,3,25-tris-ethoxycarboxylate
36) 23(R),25(S)-1α,25-dihydroxy-22-homomethylene-cholest-5-ene-26,23-lactone-1,3,25-tris-ethoxycarboxylate
37) 23(S),25(R)-1α,25-dihydroxy-22-homomethylene-cholesta-5,7-diene-26,23-lactone-1,3,25-tris-ethoxycarboxylate
38) 23(R),25(R)-1α,25-dihydroxy-22-homomethylene-cholesta-5,7-diene-26,23-lactone-1,3,25-tris-ethoxycarboxylate
39) 23(S),25(S)-1α,25-dihydroxy-22-homomethylene-cholesta-5,7-diene-26,23-lactone-1,3,25-tris-ethoxycarboxylate
40) 23(R),25(S)-1α,25-dihydroxy-22-homomethylene-cholesta-5,7-diene-26,23-lactone-1,3,25-tris-ethoxycarboxylate According to the present invention, as the preferable compounds, provided are the 1α,25-dihydroxy-26-homomethylene-vitamin $D_3$-26,23-lactones having the formula (III),

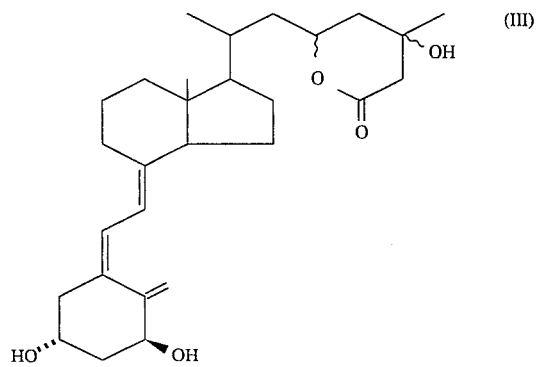

the stereoisomers thereof at the 23- and/or 25-positions or any mixtures thereof, especially 23(S),25(R)-1α,25-dihydroxy-26-homomethylene-vitamin $D_3$-26,23-lactone compounds which are compounds having an asymmetric center at C-23 of an (S) configuration and an asymmetric center at C-25 of an (R) configuration. These lactone derivatives are expected to be useful as vitamin-$D_3$ derivative type pharmaceuticals useful as agents for promotion of bone formation etc.

The 1α,25-dihydroxy-26-homomethylene-vitamin $D_3$-26,23-lactones of the above-mentioned formula (III) of the present invention may be realized by subjecting to a halogenation reaction 1α,25-dihydroxy-26-homomethylene-cholest-5-ene-26,23-lactones, which are steroid compounds of the following formula (VII-c):

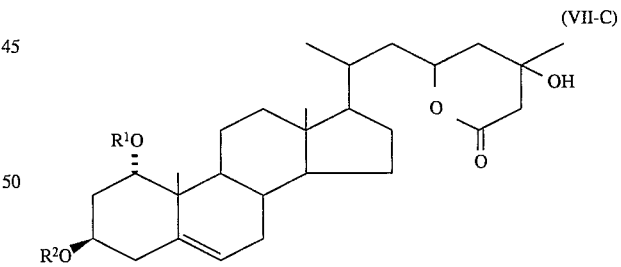

wherein, $R^1$ and $R^2$ are the same or different and are a hydrogen atom, tri($C_1$–$C_7$ hydrocarbon) silyl group, a $C$–$C_7$ acyl group, or a group forming an acetal bond together with an oxygen atom of a hydroxyl group, stereoisomers at their 23-position and/or 25-position, or any mixtures thereof, in particular, 23(S),25(R),1α,25-dihydroxy-26-homomethylene-cholest-5-ene-26,23-lactones having an asymmetric center at C-23 of an (S) configuration and an asymmetric center at C-25 of an (R) configuration, then treating them by a basic compound and, when there is a protective group of the hydroxyl group, subjecting them to a deprotecting reaction, thereby obtaining 1α,25-dihydroxy-26-homomethylene-cholesta-5,7-diene-26,23-lactones, which are steroid compounds of the following formula (V-c):

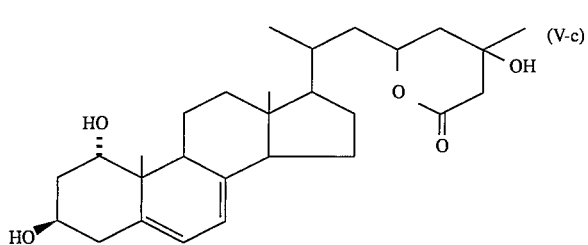

stereoisomers relating to their 23-positions and 25-positions, or any mixtures thereof, in particular, 23(S),25(R)-1α,25-dihydroxy-26-homomethylene-cholesta-5,7-diene-26,23-lactones having an asymmetric center at C-23 of an (S) configuration and an asymmetric center at C-25 of an (R) configuration, then subjecting them to a photoreaction and isomerization.

The compounds represented by the above formula (VIIc) of the present invention can be synthesized in accordance with the following scheme from the above-mentioned compound of formula (XIII). The method of synthesis of the starting substance compound (XIII) is disclosed in Japanese Unexamined Patent Publication (Kokai) No. 62-175496.

In the above-mentioned scheme, $R^1$ and $R^2$ are the same or different and are a hydrogen atom, tri($C_1$–$C_7$ hydrocarbon) silyl group, a $C_2$–$C_7$ acyl group, or a group forming an acetal bond together with an oxygen atom of a hydroxyl group.

Further, according to the present invention, it is possible to synthesize the compound (V-c) by the following steps:

(Step 1)

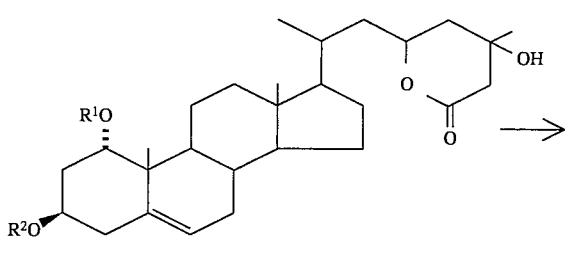

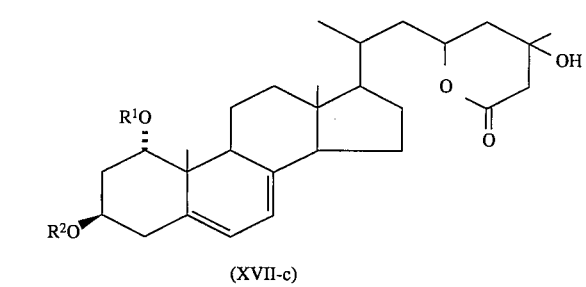

(Step 2)

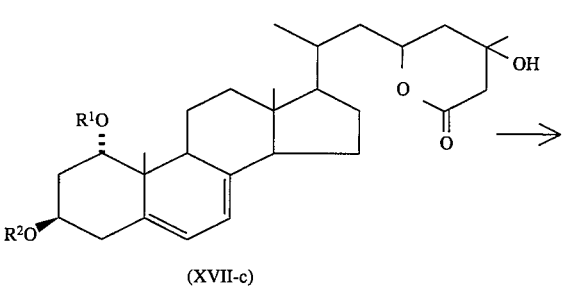

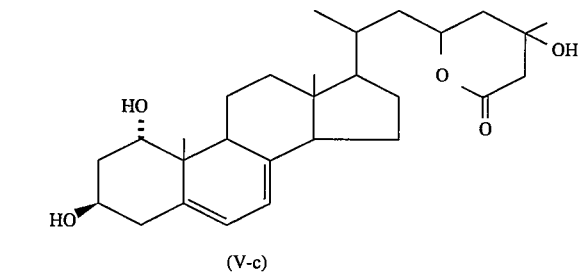

-continued
(Step 3)

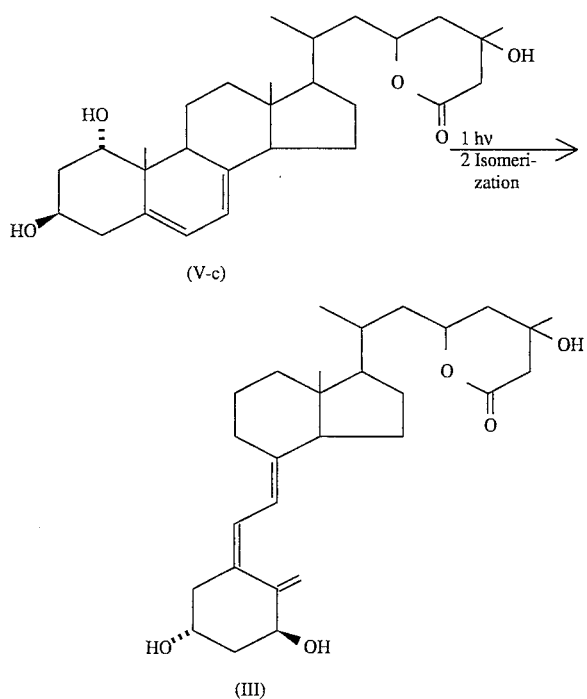

In the above scheme, $R^1$ and $R^2$ are the same or different and are a hydrogen atom, tri($C_1$–$C_7$ hydrocarbon) silyl group, a $C_2$–$C_7$ acyl group, or a group forming an acetal bond together with an oxygen atom of a hydroxyl group.

In the above formulas (VII-c) when $R^1$ or $R^2$ represents a tri($C_1$–$C_7$ hydrocarbon) silyl group, as specific examples, mention may be made of the trimethylsilyl, triethylsilyl, and t-butyldimethyl silyl groups and other tri($C_1$–$C_4$ alkyl) silyls; the t-butyldiphenylsilyl group and other diphenyl ($C_1$–$C_4$) alkylsilyls; the tribenzylsilyl group, or dimethyl-(2,4,6-tri-t-butylphenoxy)silyl group, etc. as preferable examples.

In the above formulas (VII-c) when $R^1$ or $R^2$ represents a $C_1$–$C_7$ acyl group, as specific examples, mention may be made of acetyl, propionyl, n-butyryl, iso-butyryl, n-valeryl, iso-valeryl, caproyl, enanthyl, benzoyl, methoxycarbonyl, ethoxycarbonyl, benzyloxycarbonyl, etc. Among these, $C_2$–$C_6$ acyl groups, for example, acetyl, n- or iso-butyl, benzoyl, methoxycarbonyl, and ethoxycarbonyl are preferable.

In the above formulas (VII-c) when $R^1$ or $R^2$ represents a group forming an acetal bond with the oxygen atom of a hydroxyl group, as specific examples, mention may be made of the methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, 4-(4-methoxytetrahydropyranyl) groups, the 5,6-dimethyl-3-oxa-2-bicyclo[3.1.0]hex-4-yl group, etc. Among these, the methoxymethyl, (2-methoxyethoxy)methyl, benzyloxymethyl, and 2-tetrahydropyranyl groups are preferable.

Next, the process of production of the compounds of the above-mentioned formulae (V-c) and (III) of the present invention will be explained.

In step 1, the compound (XVII-c) is obtained by causing the compound (IV-c) to undergo a halogenation reaction by an N-bromoimide, then is made to undergo dehydrohalogenation. As the N-bromoimide which can be used in the halogenation reaction, several may be mentioned, but preferably use is made of N-bromosuccinimide and 1,3-dibromo-5,5-dimethyl-hydantoin. The halogenation reaction is performed in a usual organic solvent. For example, use may be made of cyclohexane, n-hexane, carbon tetrachloride, and mixtures of the same, but use may be made of any solvent even other than these solvents so long as they do not have an adverse effect on the reaction. The reaction time and the reaction temperature are not particularly limited, but usually the reaction is performed under heating of 50° to 120° C. and ended in from 10 minutes to 3 hours. In the following dehydrohalogenation reaction, as the reagent for the dehydrohalogenation, several may be mentioned, such as organic amines, but preferably use is made of s-collidine or tetra-n-butylammoniumfluoride. The dehydrohalogenation reaction is performed in a usual organic solvent. For example, use may be made of toluene, xylene, tetrahydrofuran, methylene chloride, or mixtures of the same, but any solvent may be used in addition to these solvents so long as they do not have an adverse effect on the reaction. The reaction time and the reaction temperature are not particularly limited, but usually the reaction is performed under 0° to 160° C. and ended in from 10 minutes to 3 hours.

In step 2, the compound (V-c) is obtained by removing the protecting groups of the hydroxyl groups of the compound (XVII-c). When $R^1$ and $R^2$ are silyl groups, it may be obtained by treatment by hydrogenfluoridepyridien, tetra-n-butylammonium-fluoride, etc. When an acyl group, it may be obtained by sodium hydroxide, potassium hydroxide, lithium hydroxide, and the like in aqueous solution. When $R^1$ or $R^2$ is a group forming an acetal bond together with an oxygen atom of a hydroxyl group, it may be obtained by treatment by hydrochloric acid and other acids. When $R^1$ and $R^2$ are different, it may be obtained by a combination of the above methods. The deprotecting reaction is performed in an ordinary organic solvent. For example, use may be made of ethanol, methanol, tetrahydrofuran, acetonitrile, methylene chloride, and the like and mixtures of the same. Any solvent even outside of these solvents may be used as well so long as they have no adverse effect on the reaction. The reaction temperature and the reaction time of the deprotecting reaction are not particularly limited, but the reaction may be performed at 0° to 60° C. and end within 1 to 48 hours.

In step 3, in the photoreaction of the compound (V-c) ultraviolet light is irradiated into an organic solvent to cause the reaction. As the organic solvent, mention may be made of ethanol, ethyl acetate, tetrahydrofuran, etc., but the solvents are not limited to these. As the light source of the ultraviolet light, mention may be made of a high voltage mercury lamp, a laser (254 nm, 300 nm, 350 nm), etc., but the invention is not limited to these. As the isomerization reaction, the compound may be heated at from room temperature to 120° C. and agitated for 1 hour to several days to make it react.

Further, in the present invention, there are provided 1α,25-dihydroxy-26-homomethylene-cholest-5-ene-26,23-lactones or 1α,25-dihydroxy1-26-homomethylene-cholesta-5,7-diene-23,26-lactones, which are steroid compounds of the following formula (4'):

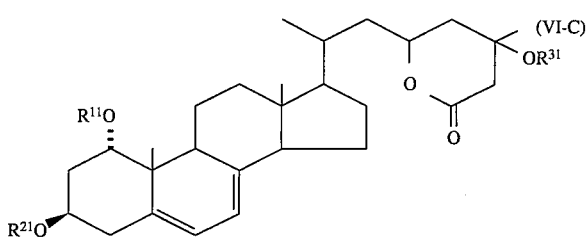

(VI-C)

wherein, $R^{11}$, $R^{21}$ and $R^{31}$ are the same or different and are a hydrogen atom, tri($C_1$–$C_7$ hydrocarbon) silyl group, $C_2$ to $C_7$ acyl group, or a group forming an acetal bond together with an oxygen atom of a hydroxyl group and the symbol " $\rightleftharpoons$ " represents that the bond is a single bond or a double bond), stereoisomers relating to their 23-position and 25-position, or mixtures of any proportions of the same.

Here, as specific examples of $R^{11}$, $R^{21}$ and $R^{31}$, the same as those described for the above-mentioned $R^1$, $R^2$ and $R^3$ may be illustrated.

As specific examples of the compounds represented by formula (4') of the present invention, mention may be made of the following. Note that these compounds are useful as intermediates for synthesis of the compounds of formula (III) which are useful as pharmaceuticals.

1) 23(S),25(R)-1α,25-dihydroxy-26-homomethylene-cholest-5-ene-26,23-lactone
2) 23(R),25(R)-1α,25-dihydroxy-26-homomethylene-cholest-5-ene-26,23-lactone
3) 23(S),25(S)-1α,25-dihydroxy-26-homomethylene-cholest-5-ene-26,23-lactone
4) 23(R),25(S)-1α,25-dihydroxy-26-homomethylene-cholest-5-ene-26,23-lactone
5) 23(S),25(R)-1α,25-dihydroxy-26-homomethylene-cholesta-5,7-diene-26,23-lactone
6) 23(R),25(R)-1α,25-dihydroxy-26-homomethylene-cholesta-5,7-diene-26,23-lactone
7) 23(S),25(S)-1α,25-dihydroxy-26-homomethylene-cholesta-5,7-diene-26,23-lactone
8) 23(R),25(S)-1α,25-dihydroxy-26-homomethylene-cholesta-57-diene-23, 26-lactone
9) 23(S),25(R) -1α,25-dihydroxy-26-homomethylene-cholest-5-ene-2 3,26-lactone-1,3-bis-t-butyldimethylsilylether
10) 23(R),25(R)-1α,25-dihydroxy-26-homomethylene-cholest-5-ene-2 3,26-lactone-1,3-bis-t-butyldimethylsilylether
11) 23(S),25(S)-1α,25-dihydroxy-26-homomethylene-cholest-5-ene-26,23-lactone-1,3-bis-t-butyldimethylsilylether
12) 23(R),25(S)-1α,25-dihydroxy-26-homomethylene-cholest-5-ene-26,23-lactone-1,3-bis-t-butyldimethylsilylether
13) 23(S),25(R)-1α,25-dihydroxy-26-homomethylene-cholesta-5,7-diene-26,23-lactone-1,3-bis-t-butyldimethylsilylether
14) 23(R),25(R)-1α,25-dihydroxy-26-homomethylene-cholesta-5,7-diene-26,23-lactone-1,3-bis-t-butyldimethylsilylether
15) 23(S),25(S)-1α,25-dihydroxy-26-homomethylene-cholesta-5,7-diene-26,23-lactone-1,3-bis-t-butyldimethylsilylether
16) 23(R),25(S)-1α,25-dihydroxy-26-homomethylene-cholesta-5,7-diene-26,23-lactone-1,3-bis-t-butyldimethylsilylether
17) 23(S),25(R)-1α,25-dihydroxy-26-homomethylene-cholest-5-ene-23,2 6-lactone-1,3-bis-methoxymethylether
18) 23(R),25 (R)-1α,25-dihydroxy-26-homomethylene-cholest-5-ene-23,2 6-lactone-1,3-bis-methoxymethylether
19) 23(S),25 (S)-1α,25-dihydroxy-26-homomethylene-cholest-5-ene-23,2 6-lactone-1,3-bis-methoxymethylether
20) 23(R),25 (S)-1α,25-dihydroxy-26-homomethylene-cholest-5-ene-23,2 6-lactone-1,3-bis-methoxymethylether
21) 23(S),25(R)-1α,25-dihydroxy-26-homomethylene-cholesta-5,7-diene-26,23-lactone-1,3-bis-methoxymethylether
22) 23(R),25(R)-1α,25-dihydroxy-26-homomethylene-cholesta-5,7-diene-26,23-lactone-1,3-bis-methoxymethylether
23) 23(S),25(S)-1α,25-dihydroxy-26-homomethylene-cholesta-5,7-diene-26,23-lactone-1,3-bis-methoxymethylether
24) 23(R),25(S)-1α,25-dihydroxy-26-homomethylene-cholesta-5,7-diene-26,23-lactone-1,3-bis-methoxymethylether
25) 23(S),25(R)-1α,25-dihydroxy-26-homomethylene-cholest-5-ene-2 3,26-lactone-1,3-bis-acetate
26) 23(R),25 (R)-1α,25-dihydroxy-26-homomethylene-cholest-5-ene-23,2 6-lactone-1,3-bis-acetate
27) 23(S),25 (S)-1α,25-dihydroxy-26-homomethylene-cholest-5-ene-23,2 6-lactone-1,3-bis-acetate
28) 23(R),25 (S)-1α,25-dihydroxy-26-homomethylene-cholest-5-ene-23,2 6-lactone-1,3-bis-acetate
29) 23(S),25(R)-1α,25-dihydroxy-26-homomethylene-cholesta-5,7-diene-26,23-lactone-1,3-bis-acetate
30) 23(R),25(R)-1α,25-dihydroxy-26-homomethylene-cholesta-5,7-diene-26,23-lactone-1,3-bis-acetate
31) 23(S),25(S)-1α,25-dihydroxy-26-homomethylene-cholesta-5,7-diene-26,23-lactone-1,3-bis-acetate
32) 23(R),25(S)-1α,25-dihydroxy-26-homomethylene-cholesta-5,7-diene-26,23-lactone-1,3-bis-acetate
33) 23(S),25(R)-1α,25-dihydroxy-26-homomethylene-cholest-5-ene-26,23-lactone-1,3-bis-ethoxycarboxylate
34) 23(R),25(R)-1α,25-dihydroxy-26-homomethylene-cholest-5-ene-26,23-lactone-1,3-bis-ethoxycarboxylate
35) 23(S),25(S)-1α,25-dihydroxy-26-homomethylene-cholest-5-ene-26,23-lactone-1,3-bis-ethoxycarboxylate
36) 23(R),25(S)-1α,25-dihydroxy-26-homomethylene-cholest-5-ene-26,23-lactone-1,3-bis-ethoxycarboxylate
37) 23(S),25(R)-1α,25-dihydroxy-26-homomethylene-cholesta-5,7-diene-26,23-lactone-1,3-bis-ethoxycarboxylate
38) 23(R),25(R)-1α,25-dihydroxy-26-homomethylene-cholesta-5,7-diene-26,23-lactone-1,3-bis-ethoxycarboxylate
39) 23(S),25(S)-1α,25-dihydroxy-26-homomethylene-cholesta-5,7-diene-26,23-lactone-1,3-bis-ethoxycarboxylate
40) 23(R),25(S)-1α,25-dihydroxy-26-homomethylene-cholesta-5,7-diene-26,23-lactone-1,3-bis-ethoxycarboxylate
41) 23(S),25(R)-1α,25-dihydroxy-22,26-dihomomethylene-cholest-5-ene-26,23-lactone
42) 23(R),25(R)-1α,25-dihydroxy-22,26-dihomomethylene-cholest-5-ene-26,23-lactone
43) 23(S),25(S)-1α,25-dihydroxy-22,26-dihomomethylene-cholest-5-ene-26,23-lactone
44) 23(R),25(S)-1α,25-dihydroxy-22,26-dihomomethylene-cholest-5-ene-26,23-lactone
45) 23(S),25(R)-1α,25-dihydroxy-22,26-dihomomethylene-cholesta-5,7-diene-26,23-lactone 46) 23(R),25(R)-1α,25-dihydroxy-22,26-dihomomethylene-cholesta-5,7-diene-23,2 6-lactone
47) 23(S),25(S)-1α,25-dihydroxy-22,26-dihomomethylene-cholesta-5,7-diene-26,23-lactone
48) 23(R),25(S)-1α,25-dihydroxy-22,26-dihomomethylene-cholesta-5,7-diene-26,23-lactone
49) 23(S),25(R)-1α,25-dihydroxy-22,26-dihomomethylene-cholest-5-ene-26,23-lactone-1,3-bis-t-butyldimethylsilyl ether
50) 23(R),25(R)-1α,25-dihydroxy-22,26-dihomomethylene-cholest-5-ene-26,23-lactone-1,3-bis-t-butyldimethylsilyl ether
51) 23(S),25(S)-1α,25-dihydroxy-22,26-dihomomethylene-cholest-5-ene-26,23-lactone-1,3-bis-t-butyldimethylsilyl ether
52) 23(R),25(S)-1α,25-dihydroxy-22,26-dihomomethylene-cholest-5-ene-26,23-lactone-1,3-bis-t-butyldimethylsilyl ether
53) 23(S),25(R)-1α,25-dihydroxy-22,26-dihomomethylene-cholesta-5,7-diene-26,23-lactone-1,3-bis-t-butyldimethylsilyl ether
54) 23(R),25(R)-1α,25-dihydroxy-22,26-dihomomethylene-cholesta-5,7-diene-26,23-lactone-1,3-bis-t-butyldimethylsilyl ether
55) 23(S),25(S)-1α,25-dihydroxy-22,26-dihomomethylene-cholesta-5,7-diene-26,23-lactone-1,3-bis-t-butyldimethylsilyl ether
56) 23(R),25(S)-1α,25-dihydroxy-22,26-dihomomethylene-cholesta-5,7-diene-26,23-lactone-1,3-bis-t-butyldimethylsilyl ether
57) 23(S),25(R)-1α,25-dihydroxy-22,26-dihomomethylene-cholest-5-ene-26,23-lactone-1,3-bis-methoxymethyl ether
58) 23(R),25(R)-1α,25-dihydroxy-22,26-dihomomethylene-cholest-5-ene-26,23-lactone-1,3-bis-methoxymethyl ether
59) 23(S),25(S)-1α,25-dihydroxy-22,26-dihomomethylene-cholest-5-ene-26,23-lactone-1,3-bis-methoxymethyl ether
60) 23(R),25(S)-1α,25-dihydroxy-22,26-dihomomethylene-cholest-5-ene-26,23-lactone-1,3-bis-methoxymethyl ether
61) 23(S),25(R)-1α,25-dihydroxy-22,26-dihomomethylene-cholesta-5,7-diene-26,23-lactone-1,3-bis-methoxymethyl ether
62) 23(R),25(R)-1α,25-dihydroxy-22,26-dihomomethylene-cholesta-5,7-diene-26,23-lactone-1,3-bis-methoxymethyl ether
63) 23(S),25(S)-1α,25-dihydroxy-22,26-dihomomethylene-cholesta-5,7-diene-26,23-lactone-1,3-bis-methoxymethyl ether
64) 23(R),25(S)-1α,25-dihydroxy-22,26-dihomomethylene-cholesta-5,7-diene-26,23-lactone-1,3-bis-methoxymethyl ether
65) 23(S),25(R)-1α,25-dihydroxy-22,26-dihomomethylene-cholest-5-ene-26,23-lactone-1,3-bis-acetate
66) 23(R),25(R)-1α,25-dihydroxy-22,26-dihomomethylene-cholest-5-ene-26,23-lactone-1,3-bis-acetate
67) 23(S),25(S)-1α,25-dihydroxy-22,26-dihomomethylene-cholest-5-ene-26,23-lactone-1,3-bis-acetate
68) 23(R),25(S)-1α,25-dihydroxy-22,26-dihomomethylene-cholest-5-ene-26,23-lactone-1,3-bis-acetate
69) 23(S),25(R)-1α,25-dihydroxy-22,26-dihomomethylene-cholesta-5,7-diene-26,23-lactone-1,3-bis-acetate
70) 23(R),25(R)-1α,25-dihydroxy-22,26-dihomomethylene-cholesta-5,7-diene-26,23-lactone-1,3-bis-acetate
71) 23(S),25(S)-1α,25-dihydroxy-22,26-dihomomethylene-cholesta-5,7-diene-26,23-lactone-1,3-bis-acetate
72) 23(R),25(S)-1α,25-dihydroxy-22,26-dihomomethylene-cholesta-5,7-diene-26,23-lactone-1,3-bis-acetate
73) 23(S),25(R)-1α,25-dihydroxy-22,26-dihomomethylene-cholest-5-ene-26,23-lactone-1,3-bis-ethoxycarboxylate
74) 23(R),25(R)-1α,25-dihydroxy-22,26-dihomomethylene-cholest-5-ene-26,23-lactone-1,3-bis-ethoxycarboxylate
75) 23(S),25(S)-1α,25-dihydroxy-22,26-dihomomethylene-cholest-5-ene-26,23-lactone-1,3-bis-ethoxycarboxylate
76) 23(R),25(S)-1α,25-dihydroxy-22,26-dihomomethylene-cholest-5-ene-26,23-lactone-1,3-bis-ethoxycarboxylate
77) 23(S),25(R)-1α,25-dihydroxy-22,26-dihomomethylene-cholesta-5,7-diene-26,23-lactone-1,3-bis-ethoxycarboxylate
78) 23(R),25(R)-1α,25-dihydroxy-22,26-dihomomethylene-cholesta-5,7-diene-26,23-lactone-1,3-bis-ethoxycarboxylate
79) 23(S),25(S)-1α,25-dihydroxy-22,26-dihomomethylene-cholesta-5,7-diene-26,23-lactone-1,3-bis-ethoxycarboxylate
80) 23(R),25(S)-1α,25-dihydroxy-22,26-dihomomethylene-cholesta-5,7-diene-26,23-lactone-1,3-bis-ethoxycarboxylate The compounds according to the present invention can be administered to a patient in various manners, orally, as a suppository, percutaneously, nasally, as a hypodermical, intramuscular, intravenous, or arterial administration etc.

For the oral administration, the compounds according to the present invention can be formulated as a solid preparation or liquid preparation. As the preparations, a tablet, pill, powder, granule, liquid, suspension, or capsule. When the tablet is prepared, conventional additives including an excipient such as lactose, starch, calcium carbonate, crystalline cellulose, or silicic acid; a binder such as carboxymethyl cellulose, methyl cellulose, calcium phosphate, or polyvinyl pyrrolidone; a disintegrator such as sodium alginate, sodium bicarbonate, sodium lauryl sulfate, stearic acid monoglyceride; a lubricant oil such as glycerol; an absorbent such as kaolin, colloidal silica; a lubricant such as talc, particulate boric acid; etc are used in a conventional manner. The pill, powder or granule can also be formulated using the similar additives in a conventional manner.

The liquid preparations in the form of, for example, a solution and a suspension can also be formulated in a conventional manner. As the carrier, mention may be made of glycerol esters such as tricaprylin, triacetin, iodinated opium oil fatty acid ester; water; alcohols such as ethanol; oily bases such as liquid paraffin, coconut oil, soybean oil, sesame oil, corn oil.

The above-mentioned powder, granules, liquid preparations can be encapsuled with a capsule such as gelatin.

The pharmaceutically acceptable carriers herein used also contain conventionally and optionally usable adjuvants, flavors, stabilizers or preservatives.

As the form of medicaments for percutaneous administration, mention may be made of an ointment, cream, lotion, liquid formulation, etc.

As the bases for ointments, mention may be made of fatty oils such as castor oil, olive oil, sesame oil, safflower oil; lanolin; white, yellow or hydrophilic vaseline; wax; higher alcohols such as oleyl alcohol, isostearyl alcohol, octyldodecanol, hexyldecanol; glycols such as glycerin, diglycerin, ethylene glycol, propylene glycol, sorbitol, 1,3-butanediol. As the solubilizing agent for the compounds according to the present invention, ethanol, dimethylsulfoxide, polyethylene glycol etc. may be used. Furthermore, if necessary, preservatives such as paraoxybenzoic esters, sodium benzoate, salicylic acid, sorbic acid, boric acid; antioxidants such as butylhydroxy anisole, dibutylhydroxy toluene may be used.

Furthermore, to accelerate the percutaneous absorption, absorption accelerators such as diisopropyl adipate, diethyl sebacate, ethyl caproate, ethyl laurate may be added. To stabilize, the present compound may be used in the form of an inclusion compound with, for example, α, β or γ-cyclodextrin or methylated cyclodextrin.

The ointment may be produced in a conventional manner. As the cream preparations, an oil-in-water type cream is preferable for stabilizing the present compound. As the bases thereof, mention may be made of the fatty oils, higher alcohols, glycols, as mentioned above. Furthermore, emulsifying agents such as diethylene glycol, propylene glycol, sorbitan monofatty acid esters, polysolvate 80, sodium lauryl sulfate may be used. Furthermore, if necessary, the preservatives, antioxidants, as mentioned above, may be added. In addition, as in the case of the ointments, the present compounds may be used in the form of an inclusion compound with cyclodextrin, methylated cyclodextrin. The cream preparations may be prepared in a conventional manner.

As the lotion preparations, mention may be made of suspensions, emulsions, solution type lotion preparations.

The suspension type lotion preparations can be obtained using a suspension agent such as sodium alginate, tragacanth, sodium carboxymethylcellulose and, if necessary, using antioxidants, preservatives, etc.

The emulsion type lotion preparations can be prepared, in a conventional manner, using a emulsifying agent such as sorbitan monofatty acid esters, polysorbate 80, sodium lauryl sulfate.

As the solution type lotion preparation, the alcohol based lotion is preferable and may be prepared, in a conventional manner, using an alcohol such as ethanol. As the liquid preparations, the present compounds are dissolved in an alcohol (e.g. ethanol) solution, followed by adding, if necessary, the above-mentioned antioxidants and preservatives.

In addition to the above-mentioned preparation forms, dermatologic pastes, poultices, aerosols may be used. These preparations may also be prepared in a conventional manner.

The preparation for nasal administration may be in the form of a liquid or powder composition. As the bases for the liquid composition, water, saline, phosphate buffers, acetate buffers can be used and furthermore may contain surfactants, antioxidants, stabilizers, preservatives, viscosity-providing agents. As the bases for the powder preparations, water absorbable bases are preferable. Examples of such bases are easily water-soluble polyacrylate salts such as sodium polyacrylate, potassium polyacrylate, ammonium polyacrylate; cellulose lower alkyl ethers such as methyl cellulose, hydroxyethyl cellulose, hydroxypropyl cellulose, sodium carboxymethyl cellulose, polyethylene glycol, polyvinylpyrrolidone, amylose, pullulan, water-slightly soluble celluloses such as crystalline cellulose, α-cellulose, sodium crosslinked carboxymethyl cellulose; starches such as hydroxypropyl starch, carboxymethyl starch, crosslinked starch, amylose, amylopectin, pectin; proteins such as gelatin, casein, sodium casein; gums such as arabic gum, tragacanth gum, glucomannan; crosslinked vinyl polymers such as polyvinylpolypyrrolidone, crosslinked polyacrylic acid and a salt thereof, crosslinked polyvinyl alcohol, polyhydroxyethyl methacrylate. These bases may be used in any mixture thereof. Furthermore, the powder preparations may optionally contain antioxidants, coloring agents, preservatives, antiseptics, corrigents. These liquid preparations, powder preparations may be applied by using, for example, a spraying device.

The preparations for injection administration are generally provided as an axenic aqueous or non-aqueous liquid, suspension or emulsion. The non-aqueous solution or suspension uses, as a pharmaceutically acceptable carrier, propylene glycol, polyethylene glycol, vegetable oils such as olive oil, injectable organic esters such as ethyl oleate, iodinated poppy oil fatty acid ester, etc. These preparation may also contain adjuvants such as preservatives, humectants, emulsifiers, dispersing agents, stabilizers and may be in the sustained form release. The preparations in the forms of solutions, dispersions and emulsions can be sterilized by filtering the same through, for example, a bacteria retaining filter, by formulating a bactericide or by irradiation. Alternatively, an axenic solid preparation is formulated and, immediately before the use thereof, the solid preparation is dissolved in an axenic water or an axenic solvent for injection. Furthermore, as mentioned above, the present compounds are usable as an inclusion compound formed with an α-, β- or γ-cyclodextrin or methylated cyclodextrin etc. Furthermore, the present compounds can be used in a lipo form as an injection agent.

The pharmaceutically effective amount of the present compounds to be administered to a patient depends upon, for example, the administration method, ages, sexuality, and the conditions of the patient, but generally about $1-10^5$ μg/kg/day, preferably $10-10^4$ μg/kg/day is administered.

EXAMPLES

The present invention will now be further illustrated by, but is by no means limited to, the following Examples.

Example 1-1

Synthesis of (23S,25R)-1α,25-dihydroxy-22-homomethylene-cholest-5-ene-26,23-lactone

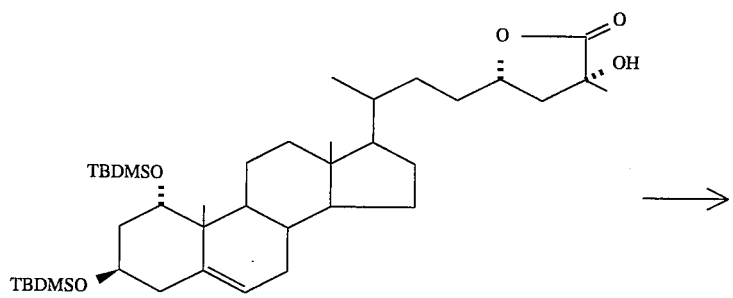

1a

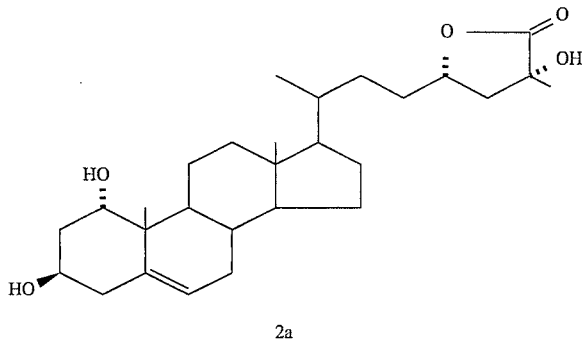

2a

A 15 ml amount of acetonitrile and 15 ml of pyridine were placed in a 200 ml eggplant shaped flask and were agitated while being ice-cooled. To this was added 30 ml of hydrogen fluoride-pyridine.

A 458 mg amount of (23S,25R)-1α,25-dihydroxy-22-homomethylene-cholest-5-ene-26,23-lactone-1,3-bis-t-butyldimethylsilyl ether (1a) was dissolved in 5 ml of acetonitrile and 3 ml of pyridine and placed in the above reaction solution. The mixture was agitated under ice-cooling for 1 hour, then was returned to room temperature and agitated for 1 day.

The reaction solution was poured into 400 ml of ethyl acetate and 250 ml of water and neutralized by sodium bicarbonate, then the organic layer was washed two times by a saturated saline solution. This was dried on anhydrous magnesium sulfate, the desiccant was filtered out, and the solvent was distilled off under reduced pressure to obtain 400 mg of a crude substance. This was refined by a silica gel column (IR-60 Silica, 150 g hexane/ethyl acetate=1/2 to 1/3) to obtain the target (23S,25R)-1α,25-dihydroxy-22-homomethylene-cholest-5-ene-26,23-lactone (2a) in an amount of 284 mg (92% yield ).

H-NMR (CDCl$_3$, δppm) 0.69 (s, 3H), 0.94 (d, 3H, J=6.6 Hz), 1.04 (s, 3H), 1.51 (s, 3H), 1.0–2.5 (m, 27H), 3.85 (brs, 1H), 3.9–4.1 (m, 1H), 4.4–4.5 (m, 1H), 5.60 (dlike, 1H)

Example 1-2

Synthesis of (23S,25R)-1α,25-dihydroxy-22-homomethylene-cholest-26,23-lactone

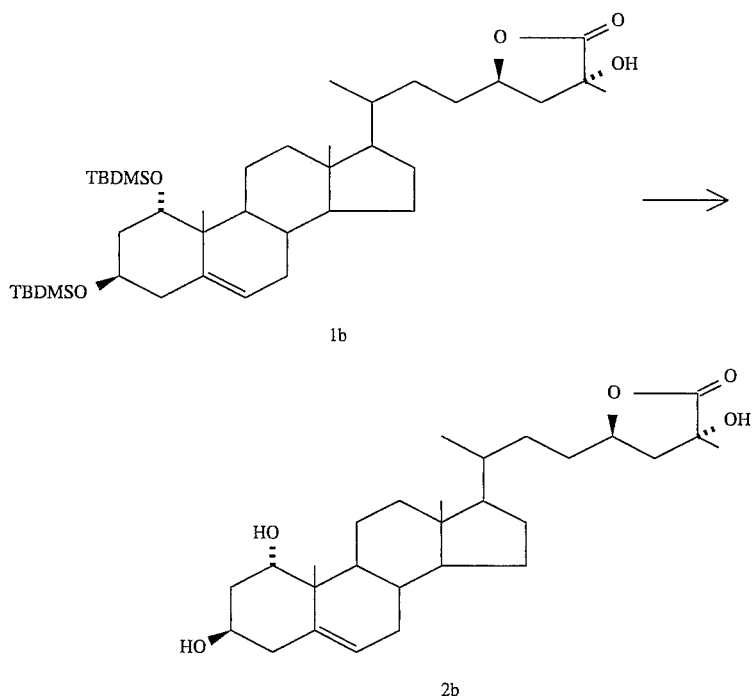

A 255 mg amount of (23R,25R)-1α,25-dihydroxy-22-homomethylene-cholest-5-ene-26,23-lactone-1,3-bis-t-butyldimethylsilylether (1b) was reacted in the same way to obtain (23R,25R)-1α,25-dihydroxy-22-homomethylene-cholest-26,23-lactone (2b) in an amount of 150 mg (87% yield).

$^1$H-NMR (CDCl$_3$, δ ppm) 0.69 (s, 3H), 0.94 (d, 3H, J=6.6 Hz), 1.04 (s, 3H), 1.48 (s, 3H), 1.0–2.5 (m, 27H), 3.85 (brs, 1H), 3.95–4.1 (m, 1H), 4.2–4.3 (m, 1H), 5.59 (dlike, 1H)

Example 1-3

Synthesis of (23S,25R)-1α,25-dihydroxy-22-homomethylene-cholest-5-ene-26,23-lactone-1,3,25trisethoxycarboxylate

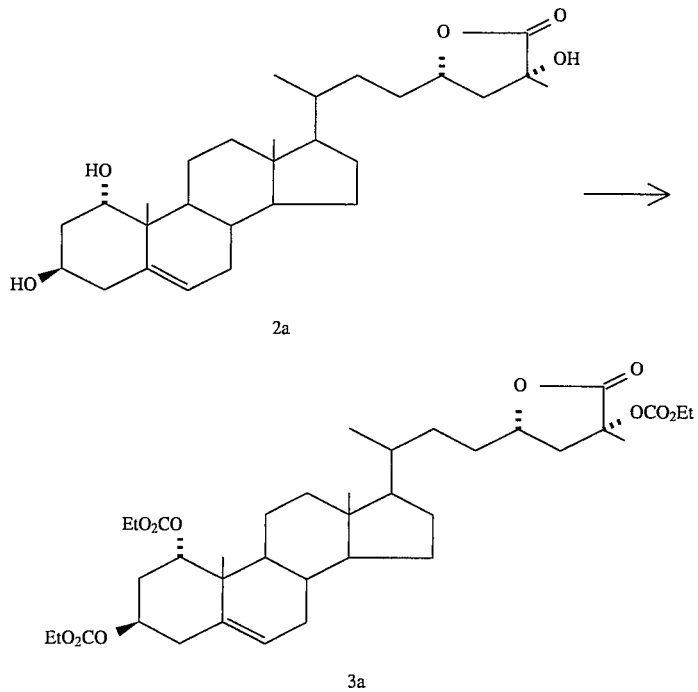

A 284 mg amount of (23S,25R)-1α,25-dihydroxy-22-homomethylene-cholest-5-ene-26,23-lactone (2a) was placed in a flask and dissolved with the addition of 20 ml of methylene chloride. To this was added 2.11 g of 4dimethylaminopyridine. Further, 84 ml of ethyl chloroformate was added drop-wise and the mixture was agitated at room temperature for one night. To the reaction solution was added 20 ml of water and 50 ml of ethyl acetate to extract it. The organic layer was washed two times each with 10 ml of a saturated aqueous solution of potassium hydrogen sulfate, a saturated solution of sodium bicarbonate, and a saturated saline solution, then was dried on anhydrous magnesium sulfate, then the desiccant was filtered out and the solvent was distilled off under reduced pressure to obtain 370 mg of a crude substance. This was refined by a silica gel column (IR-60 Silica, 100 g hexane/ethyl acetate=4/1) to obtain the target (23S,25R)-1α,25-dihydroxy-22-homomethylene-cholest-5-ene-26,23-lactone-1,3,25-trisethoxycarboxylate (3a) in an amount of 341 mg (82% yield).

$^1$H-NMR (CDCl$_3$, δ ppm) 0.67 (s, 3H), 0.92 (d, 3H, J=6.26 Hz), 1.08 (s, 3H), 1.64 (s, 3H), 1.0–2.8 (m, 33H), 4.1–4.3 (m, 6H), 4.6–4.7 (m, 1H), 4.75–4.95 (m, 1H), 4,91 (brs, 1H), 5.56 (dlike, 1H)

Example 1-4

Synthesis of (23R,25R)-1α,25-dihydroxy-22-homomethylene-cholest-5-ene-26,23-lactone-1,3,25-trisethoxycarboxylate

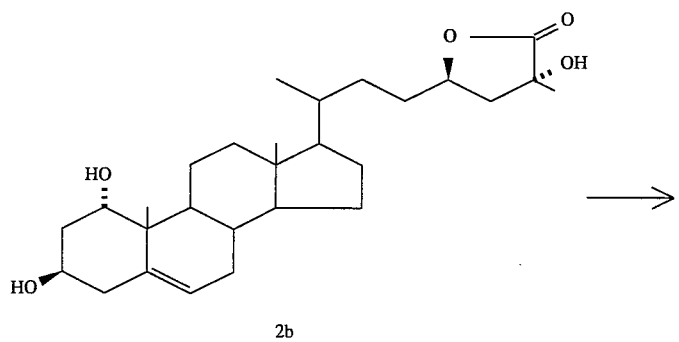

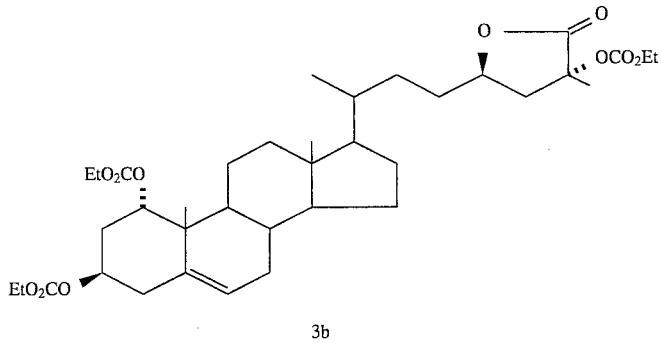

3b

A 150 mg amount of (23R,25R)-1α,25-dihydroxy-22-homomethylene-cholest-5-ene-26,23-lactone (2b) was similarly treated to obtain (23R,25R)-1α,25-dihydroxy-22-homomethylene-cholest-5-ene-26,23-lactone-1,3,25-trisethoxycarboxylate (3b) in an amount of 202 mg (91% yield).

$^1$H-NMR (CDCl$_3$, δ ppm) 0.67 (s, 3H), 0.93 (d, 3H, J=6.6 Hz), 1.08 (s, 3H), 1.60 (s, 3H), 1.0–2.6 (m, 33H), 4.1–4.3 (m, 6H), 4.2–4.4 (m, 1H), 4.75–4.9 (m, 1H), 4.91 (brs, 1H), 5.55 (dlike, 1H)

Example 1-5

Synthesis of (23S,25R)-1α,25-dihydroxy-22-homomethylene-cholesta-5,7-diene-26,23-lactone-1,3,25-trisethoxycarboxylate

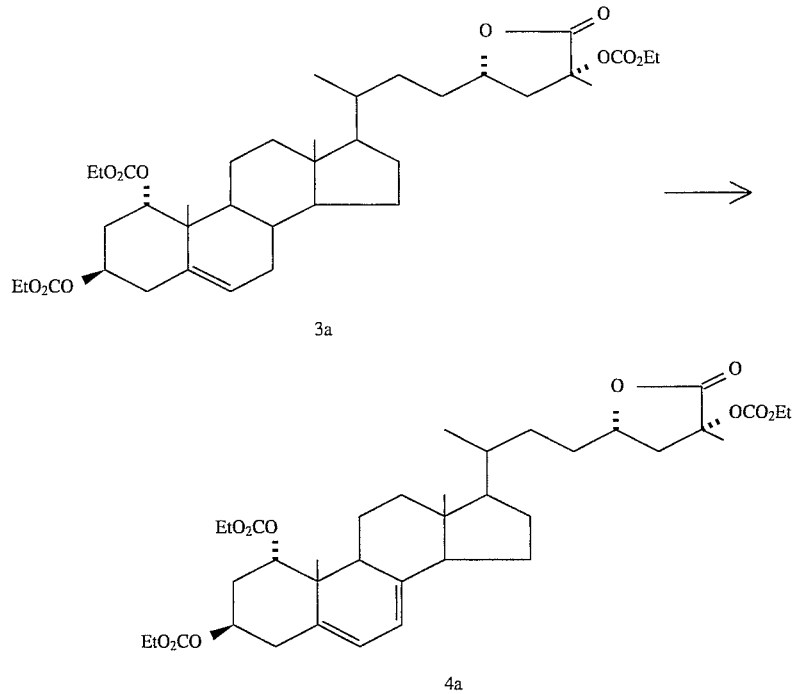

A 377 mg amount of (23S,25R)-1α,25-dihydroxy-22-homomethylene-cholest-5-ene-26,23-lactone-1,3,25-trisethoxycarboxylate (3a) was placed in a flask and heated and dissolved with the addition of 7.5 ml of hexane and 30 ml of carbon tetrachloride. To this was added 85.4 mg of 1,3-dibromo-5,5-dimethyl-hydantoin, after which the mixture was heated and agitated for 30 minutes. The reaction solution was allowed to cool, then the insolubles were removed and the solvent was distilled off under reduced pressure. The resultant residue was dissolved in 7.5 ml of tetrahydrofuran. To this was added 479 mg of tetrabutylammoniumfluoride dissolved in 7.5 ml of tetrahydrofuran, then the mixture was agitated at room temperature for 30 minutes. The reaction solution was poured into 80 ml of ethyl acetate and 30 ml of water and mixed well, then separated. The organic layer was washed two times with 20 ml each of a saturated solution of sodium bicarbonate and a saturated saline solution, then was dried on anhydrous magnesium sulfate, then the desiccant was filtered out, the solvent distilled off under reduced pressure, and the resultant residue refined by a silica gel column (IR-60 Silica, 100 g hexane/ethyl acetate=2/1 to 1/1) to obtain the target (23S,25R)-1α, 25-dihydroxy-22-homomethylene-cholesta-5,7-diene-26, 23-lactone-1,3,25-trisethoxycarboxylate (4a) in an amount of 246 mg (73% yield).

$^1$H-NMR (CDCl$_3$, δ ppm) 0.60 (s, 3H), 0.93 (d, 3H, J=6.6 Hz), 0.99 (s, 3H), 1.30 (t, 9H, J=8.3 Hz), 1.62 (s, 3H), 1.0–2.9 (m, 24H), 4.1–4.3 (m, 6H), 4.6–4.7 (m, 1H), 4.82

(brs, 1H), 4.85–4.95 (m, 1H), 5.3–5.45 (m, 1H), 5.60–5.75 (m, 1H)

Example 1-6

Synthesis of (23R,25R)-1α,25-dihydroxy-22-homomethylene-cholesta-5,7-diene-26,23-lactone-1,3,25-trisethoxycarboxylate in an amount of 140 mg (70% yield).

$^1$H-NMR (CDCl$_3$, δ ppm) 0.55 (s, 3H), 0.89 (d, 3H, J=6.6 Hz), 0.94 (s, 3H), 1.54 (s, 3H), 1.0–2.8 (m, 33H), 4.05–4.20 (m, 6H), 4.2–4.3 (m, 1H), 4.78 (brs, 1H), 4.8–4.9 (m, 1H), 5.25–5.35 (m, 1H), 5.55–5.65 (m, 1H)

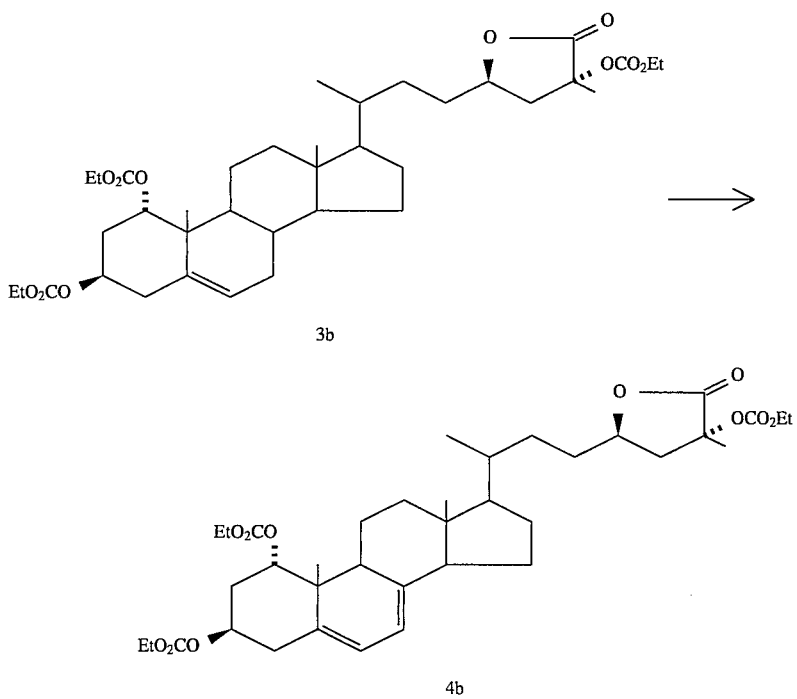

A 202 mg amount of (23R,25R)-1α,25-dihydroxy-22-homomethylene-cholest-5-ene-26,23-lactone-1,3=25-trisethoxycarboxylate (3b) was similarly treated to obtain (23R,25R)-1α,25-dihydroxy-22-homomethylene-cholesta-5,7-diene-26,23-lactone-1,3,25-trisethoxycarboxylate (4b)

Example 1-7

Synthesis of (23S,25S)-1α,25-dihydroxy-22-homomethylene-cholesta-5,7-diene-26,23-lactone

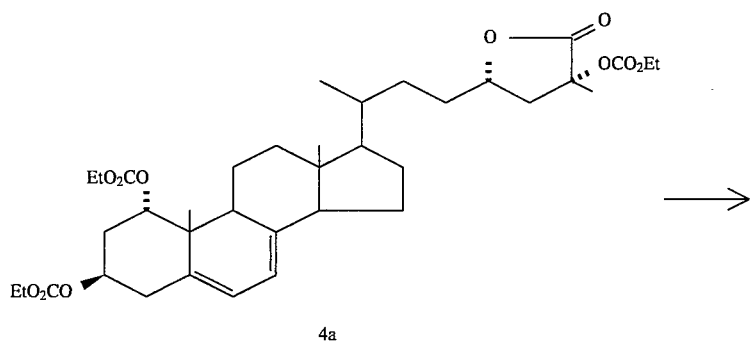

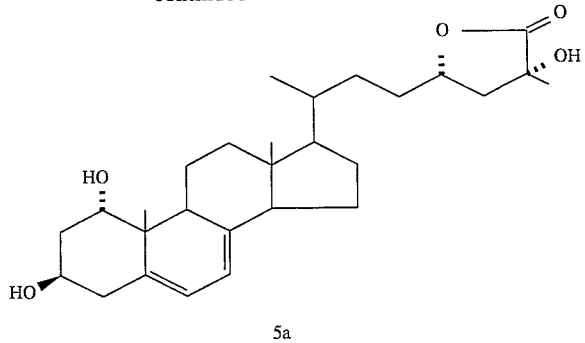

5a

A 241 mg amount of (23S,25R)-1α,25-dihydroxy-22-homomethylene-cholesta-5,7-diene-26,23-lactone-1,3,25-trisethoxycarboxylate (4a) was placed in a flask and dissolved in 20 ml of tetrahydrofuran and 10 ml of methanol. To this was added 5 ml of an aqueous solution of 4N lithium hydroxide and the mixture was agitated at room temperature in a dark place for 16 hours. To the reaction solution was added a saturated aqueous solution of potassium hydrogen sulfate to adjust the pH to about 2, then the mixture was agitated at room temperature in a dark place for 1 hour. To the reaction solution was added 5 ml of water and 5 ml of saturated saline solution, then extraction was performed with 50 ml of ethyl acetate. The organic layer was washed two times with 15 ml of saturated saline water, then was dried on anhydrous magnesium sulfate. The desiccant was filtered out and the solvent distilled off under reduced pressure to obtain 230 mg of a crude substance. This was refined by a silica gel column (IR-60 Silica, chloroform/methanol=15/1) to obtain the target (23S,25R)-1α,25-dihydroxy-22-homomethylene-cholesta-5,7-diene-26,23-lactone (5a) in an amount of 118 mg (70% yield).

$^1$H-NMR (CDCl$_3$, δ ppm) 0.63 (s, 3H), 0.95 (s, 3H), 0.96 (dlike, 3H), 1.51 (s, 3H), 1.0–2.8 (m, 25H), 3.77 (brs, 1H), 4.0–4.15 (m, 1H), 4.5–4.6 (m, 1H), 5.35–5.45 (m, 1H), 5.65–5.75 (m, 1H)

Example 1-8

Synthesis of (23R,25R)-1α,25-dihydroxy-22-homomethylene-cholesta-5,7-diene-26,23-lactone

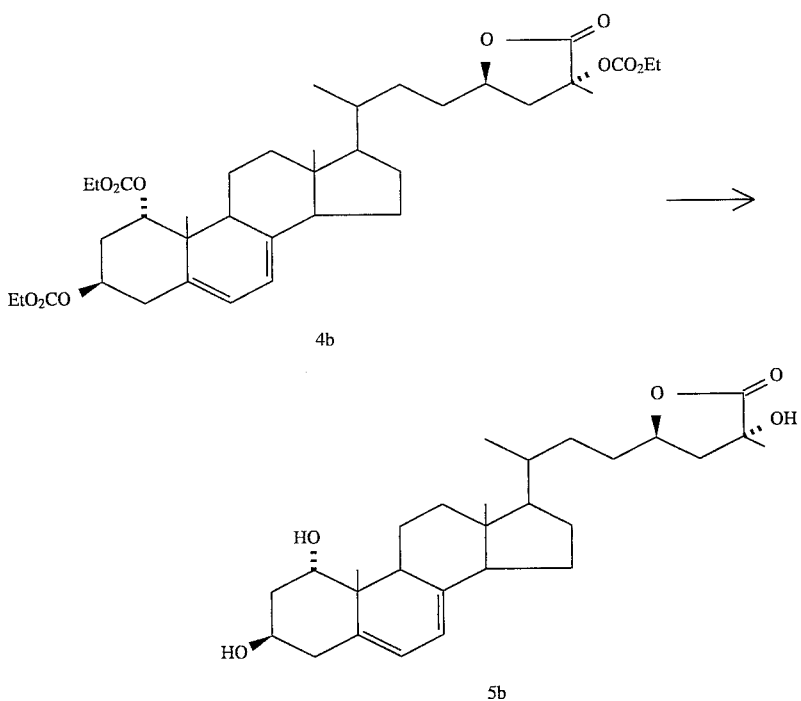

A 133 mg amount of (23R,25R)-1α,25-dihydroxy-22-homomethylene-cholesta-5,7-diene-26,23-lactone-1,3-25-trisethoxycarboxylate (4b) was similarly treated to obtain (23R,25R )-1α,25-dihydroxy-22-homomethylene-cholesta-5,7-diene-26,23-lactone (5b) in an amount of 62 mg (69% yield).

$^1$H-NMR (CDCl$_3$, δ ppm) 0.64 (s, 3H), 0.95 (s, 3H), 0.97 (dlike, 3H), 1,49 (s, 3H), 1.0–2.9 (m, 25H), 3.77 (brs, 1H), 3.95–4.1 (m, 1H), 4.25–4.3 (m, 1H), 5.35–5.45 (m, 1H), 5.7–5.8 (m, 1H)

Example 1-9

Synthesis of (23S,25R)-1α,25-dihydroxy-22-homomethylene-vitamin D₃-26,23-lactone

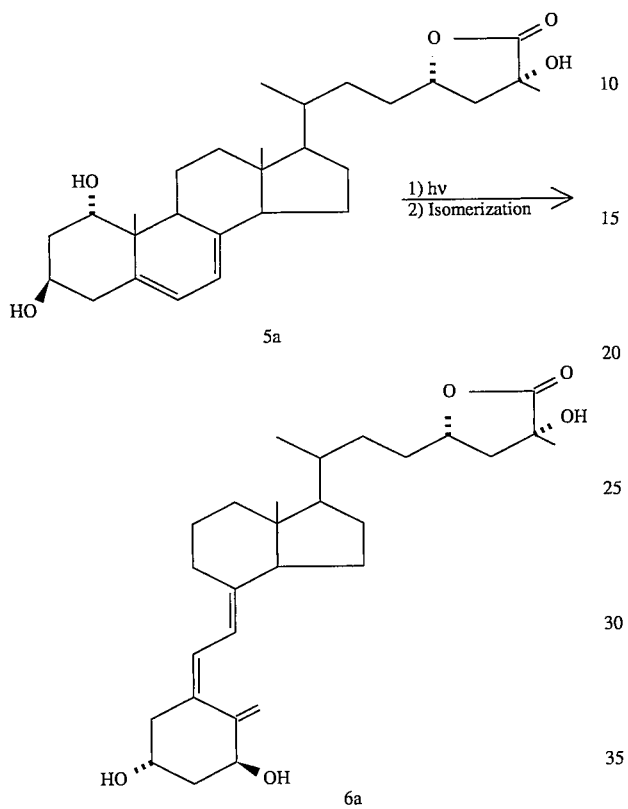

A 15.8 mg amount of (23S,25R)-1α,25-dihydroxy-22-homomethylene-cholesta-5,7-diene-26,23-lactone (5a) was placed in a quartz glass reaction vessel and dissolved with the addition of 50 ml of tetrahydrofuran. This was irradiated with 300 nm ultraviolet light for 30 minutes in an argon atmosphere. This reaction solution was transferred to a 200 ml flask and heated and refluxed at a dark place for 90 minutes. The reaction solution was allowed to cool, then was condensed to obtain 18.2 mg of a crude substance. This was refined by high pressure liquid chromatography (Zorbax, hexane/ethanol=88/11) to obtain the target (23S,25R)-1α,25-dihydroxy-22-homomethylene-vitamin D₃-26,23-lactone (6a) in an amount of 2.4 mg (15% yield).

¹H-NMR (CDCl₃, δ ppm) 0.55 (s, 3H), 0.94 (d, 3H, J=6.27 Hz), 1.1–2.9 (m, 29H), 4.10–4.20 (m, 1H), 4.30–4.40 (m, 1H), 4.40–4.50 (m, 1H), 5.00 (s, 1H), 5.33 (s, 1H), 6.01 (d, 1H, J=11.22 Hz), 6.38 (d, 1H, J=11.22 Hz)

Mass (m/e) 458 (M⁺)

Example 1-10

Synthesis of (23R,25R)-1α,25-dihydroxy-22-homomethylene-vitamin D₃-26,23-lactone

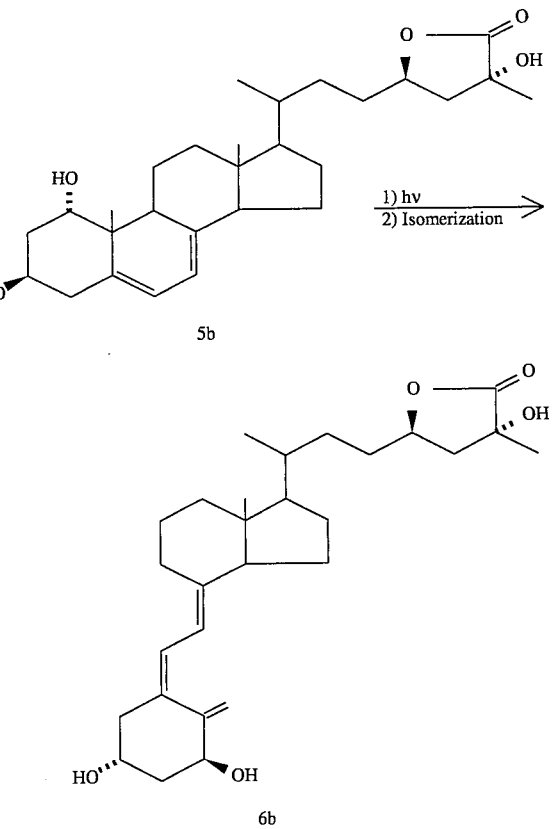

A 29 mg amount of (23R,25R)-1α,25-dihydroxy-22-homomethylene-cholesta-5,7-diene-26,23-lactone (5b) was similarly treated to obtain the target (23R,25R)-1α,25-dihydroxy-22-homomethylene-vitamin D₃-26,23-lactone (6b) in an amount of 5.0 mg (17% yield).

¹H-NMR (CDCl₃, δ ppm) 0.55 (s, 3H), 0.92 (d, 3H, J=6.27 Hz), 1.1–2.9 (m, 29H), 4.10–4.30 (m, 2H), 4.50–4.60 (m, 1H), 5.00 (s, 1H), 5.33 (s, 1H), 6.01 (d, 1H, J=11.22 Hz), 6.38 (d, 1H, J=11.22 Hz)

Mass (m/e) 458 (M⁺)

Example 2-1

Synthesis of (23S,25R)-1α,25-dihydroxy-26-homomethylene-cholest-5-ene-26,23-lactone

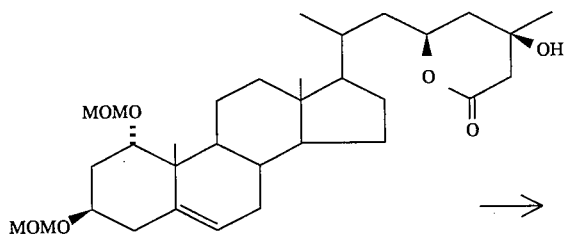

-continued

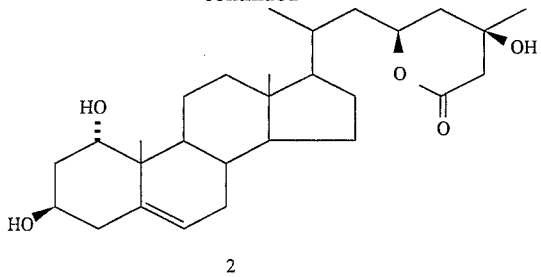

2

A 1.2 g amount of (23S,25R)-1α,25-dihydroxy-26-homomethylene-cholest-5-ene-26,23-lactone-1,3-bis-methoxymethylether (1) was placed in a flask and dissolved with the addition of 20 ml of tetrahydrofuran and 10 ml of methanol. To this was added 10 ml of 2N hydrochloric acid, then this was heated to 50° C. and agitated for 6 hours. The reaction solution was neutralized by a saturated aqueous solution of sodium bicarbonate, then extracted by the addition of 80 ml of ethyl acetate. The organic layer was washed two times with 20 ml each of water and saturated saline solution, then was dried on anhydrous magnesium sulfate, then the desiccant was filtered out and the solvent was distilled off under reduced pressure to obtain 3.5 g of a crude substance. This was refined by a silica gel column (IR-60 Silica, 150 g hexane/ethyl acetate=1/2 to 1/3) to obtain the target (23S,25R)-1α,25-dihydroxy-26-homomethylene-cholest-5-ene-26,23-lactone (2) in an amount of 0.72 g (70% yield). The results of analysis were as follows:

$^1$H-NMR (CDCl$_3$, δ ppm) 0.75 (s, 3H), 1.01 (s, 3H), 1.03 (d, 3H, J=5 Hz), 1.30 (s, 3H), 1.1–2.7 (m, 28H), 3.79 (brs, 1H), 3.8–4.0 (m, 1H), 4.7–4.8 (m, 1H), 5.48 (br, 1H)

Example 2-2

Synthesis of (23S,25R)-1α,25-dihydroxy-26-homomethylene-cholest-26,23-lactone-1,3-bis-ethoxycarboxylate

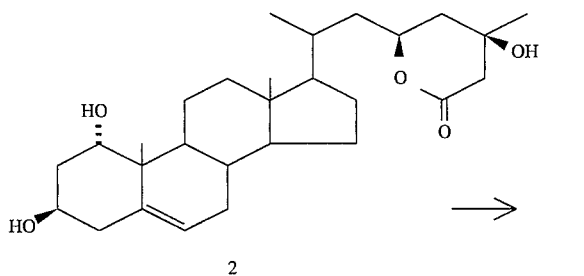

2

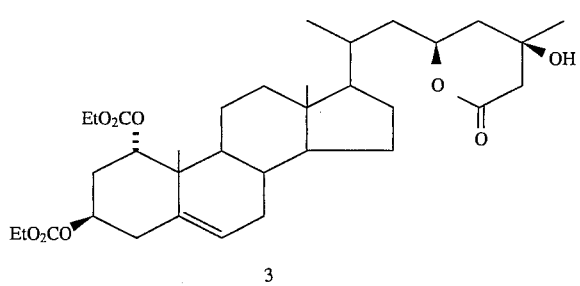

3

A 1.05 g amount of (23S,25R)-1α,25-dihydroxy-26-homomethylene-cholest-5-ene-26,23-lactone (2) was placed in a flask and dissolved with the addition of 10 ml of tetrahydrofuran and 40 ml of methylene chloride. To this was added 7.87 g of 4-dimethylaminopyridine, then 3.08 ml of ethyl chloroformate was added dropwise and the solution was agitated at room temperature one night. To the reaction solution was added 20 ml of water and 20 ml of ether, then further 100 ml of ethyl acetate was added for extraction. The organic layer was washed two times with 30 ml each of a saturated aqueous solution of potassium hydrogen sulfate and saturated saline solution, then was dried on anhydrous magnesium sulfate, then the desiccant was filtered out and the solvent was distilled off under reduced pressure to obtain 2.12 g of a crude substance. This was refined by a silica gel column (IR-60 Silica, 100 g hexane/ethyl acetate=2/1 to 1/1) to obtain the target (23S,25R)-1α,25-dihydroxy-26-homomethylene-cholest-5-ene-26,23-lactone-1,3-bisethoxycarboxylate (3) in an amount of 1.33 g (89% yield).

$^1$H-NMR (CDCl$_3$, δ ppm) 0.69 (s, 3H), 1.01 (s, 3H, J=6 Hz), 1.08 (s, 3H), 1.39 (s, 3H), 1.0–2.8 (m, 32H), 4.0–4.2 (m, 4H), 4.7–4.85 (m, 1H), 4.8–4.9 (m, 1H), 4.91 (brs, 1H), 5.54 (br, 1H)

Example 2-3

Synthesis of (23S,25R)-1α,25-dihydroxy-26-homomethylene-cholesta-5,7-diene-26,23-lactone-1,3-bisethoxycarboxylate

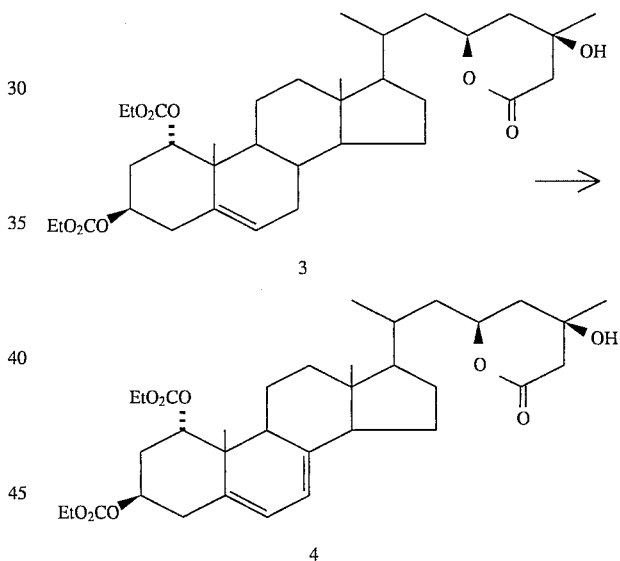

A 200 mg amount of (23S,25R)-1α,25-dihydroxy-26-homomethylene-cholest-5-ene-26,23-lactone-1,3-bisethoxycarboxylate (3) was placed in a flask and dissolved with the addition of 5 ml of hexane and 18 ml of carbon tetrachloride. To this was added 57 mg of 1,3-dibromo-5,5-dimethyl-hydantoin, then the mixture was heated and agitated for 30 minutes. The reaction solution was allowed to cool, then insolubles were removed and the solvent was distilled off under reduced pressure. The resultant residue was dissolved in 5 ml of tetrahydrofuran. To this was added 321 mg of tetrabutylammoniumfluoride dissolved in 5 ml of tetrahydrofuran, then the mixture was agitated at room temperature for 30 minutes. The reaction solution was poured into 50 ml of ethyl acetate and 20 ml water and mixed well, then the mixture was separated and the organic layer was washed two times with 20 ml of saturated saline solution. This was then dried on anhydrous magnesium sulfate, then the desiccant was filtered out and the solvent was distilled off under reduced pressure. The resultant residue was refined by a silica gel column (IR-60 Silica, 100 g hexane/ethyl acetate=2/1 to 1/1) to obtain the target (23S,25R)-1α,25-dihydroxy-26-homomethylene-cholesta-5,7-diene-26,23-lactone-1,3-bisethoxycarboxylate (4) in an amount of 180 mg (90% yield).

$^1$H-NMR (CDCl$_3$, δ ppm) 0.63 (s, 3H), 0.9–1.1 (m, 6H), 1.39 (s, 3H), 1.15–2.9 (m, 29H), 4.0–4.2 (m, 4H), 4.7–4.8 (m, 1H), 4.85 (brs, 1H), 4.85–5.05 (m, 1H), 5.3–5.4 (m, 1H), 5.65–5.75 (m, 1H)

Example 2-4

Synthesis of (23S,25R)-1α,25-dihydroxy-26-homomethylene-cholesta-5,7-diene-26,23-lactone

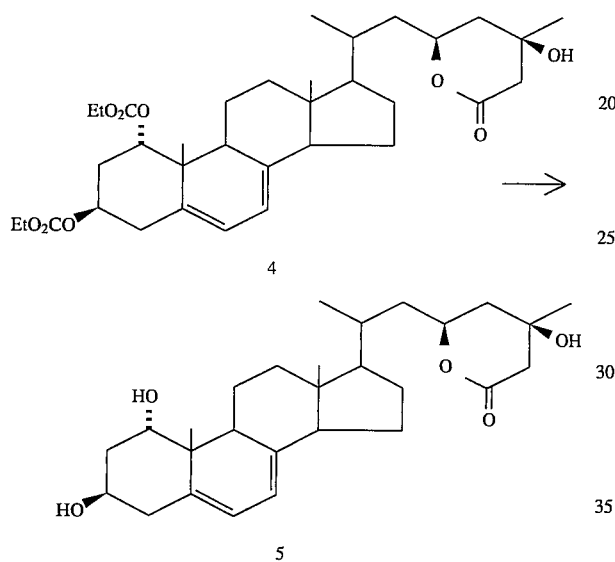

A 180 mg amount of (23S,25R)-1α,25-dihydroxy-26-homomethylene-cholesta-5,7-diene-26,23-lactone-1,3-bisethoxycarboxylate (4) was placed in a flask and dissolved in 7 ml of tetrahydrofuran and 7 ml of methanol. To this was added 3 ml of an aqueous solution of 4N lithium hydroxide and the mixture was agitated at room temperature in a dark place for 16 hours. To the reaction solution was added a saturated aqueous solution of potassium hydrogen sulfate to adjust the pH to about 2, then the mixture was agitated at room temperature in a dark place for 2 hours. To the reaction solution was added 5 ml of water and 5 ml of saturated saline solution, then extraction was performed with 50 ml of ethyl acetate. The organic layer was washed two times with 15 ml of saturated saline water, then was dried on anhydrous magnesium sulfate. The desiccant was filtered out and the solvent distilled off under reduced pressure to obtain 164 mg of a crude substance. This was refined by a silica gel column (IR-60 Silica, 50 g hexane/ethyl acetate=1/2 to 0/1) to obtain the target (23S,25R)-1α,25-dihydroxy-26-homomethylene-cholesta-5,7-diene-26,23-lactone (5) in an amount of 109 mg (82% yield).

$^1$H-NMR (CDCl$_3$, δ ppm) 0.69 (s, 3H), 0.92 (s, 3H), 1.06 (d, 3H, J=5 Hz), 1.31 (s, 3H), 2.53 (s, 2H), 1.1–2.9 (m, 23H), 3.7–4.1 (m, 2H), 4.7–4.8 (m, 1H), 5.48 (d, 1H, J=5 Hz), 5.62 (d, 1H, J=5 Hz)

Example 2-5

Synthesis of (23S,25R)-1α,25-dihydroxy-26-homomethylene-vitamin D$_3$-26,23-lactone

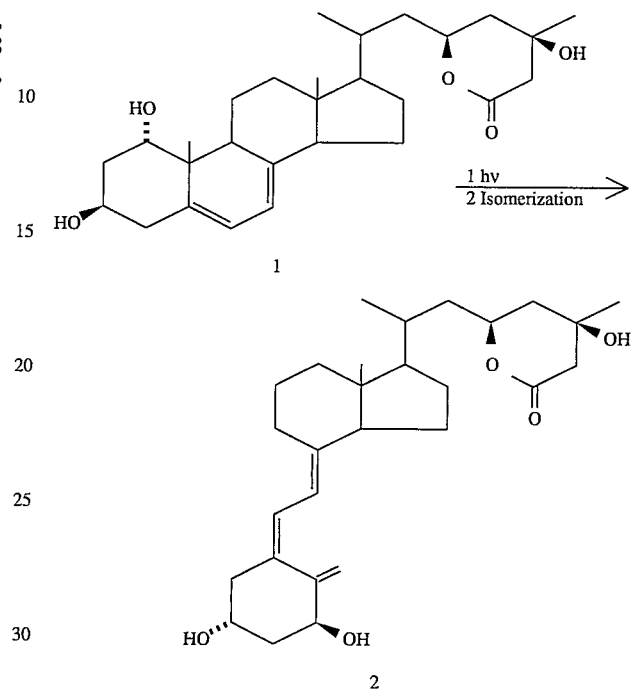

A 160 mg amount of (23S,25R)-1α,25-dihydroxy-26-homomethylene-cholesta-5,7-diene (b 1) was placed in a quartz glass reaction vessel. A 500 ml amount of tetrahydrofuran was added and 300 nm ultraviolet light was irradiated for 40 minutes in an argon atmosphere. This reaction solution was placed in a 1 liter eggplant shaped flask and heated and refluxed at a dark place in a nitrogen atmosphere for 75 minutes. This was allowed to cool at room temperature, then the solvent was distilled off under reduced pressure to obtain 190 mg of a crude substance. This was refined by high pressure liquid chromatography (Toso Silica Column, hexane/ethanol=85/15) to obtain 54 mg of the target substance (2).

Example 3-1 (Evaluation of Bone Formation)

A human osteoblast (KK-3, 18 PDL) was cultured in α-MEM (i.e., α-Minimum Essential Medium) containing 10% fetal bovine serum at 37° C. in 5% CO$_2$/95% air. After cells became confluent, the test compound at the given concentration was added in the presence of 2 mMα-glycerophosphate, and the cell culture was continued for 14 days. The cell layer was washed with physiological saline and, then, an alkaline phosphatase activity (ALP) was determined from the optical density (OD) at 415 nm. Thereafter, calcium (Ca) and phosphorus (P) were extracted with 2N HCl, followed by a quantitative determination.

The results are shown in Table 3-1.

TABLE 3-1

| Compound | Concentration (H) | Ca (μg/well) | Pi (μg/well) | ALP (ABS 415 nm) |
|---|---|---|---|---|
| Control (no compound) | — | 25.62 ± 2.45 | 17.72 ± 1.37 | 0.653 ± 0.017 |
| Example 2-5 | $1 \times 10^{-9}$ | 31.92 ± 3.90 | 21.65 ± 1.73 | 0.747 ± 0.032 |
| | $1 \times 10^{-8}$ | 62.17 ± 2.37 | 38.27 ± 1.74 | 0.790 ± 0.023 |
| | $1 \times 10^{-7}$ | 54.35 ± 2.66 | 34.22 ± 2.60 | 0.833 ± 0.020 |
| Example 1-9 | $1 \times 10^{-9}$ | 30.70 ± 1.43 | 20.85 ± 1.00 | 0.618 ± 0.014 |
| | $1 \times 10^{-8}$ | 64.33 ± 8.18 | 38.15 ± 4.03 | 0.623 ± 0.031 |
| | $1 \times 10^{-7}$ | 63.63 ± 0.57 | 38.60 ± 0.18 | 0.713 ± 0.062 |
| Example 1-10 | $1 \times 10^{-9}$ | 26.65 ± 3.05 | 19.47 ± 0.33 | 0.715 ± 0.046 |
| | $1 \times 10^{-8}$ | 25.13 ± 0.86 | 18.08 ± 0.92 | 0.724 ± 0.051 |
| | $1 \times 10^{-7}$ | 56.82 ± 3.47 | 34.92 ± 1.84 | 0.583 ± 0.064 |
| Known Compound [structure] | $1 \times 10^{-9}$ | 45.50 ± 7.94 | 28.82 ± 4.58 | 0.624 ± 0.051 |
| | $1 \times 10^{-8}$ | 42.20 ± 11.61 | 26.82 ± 6.08 | 0.604 ± 0.080 |
| | $1 \times 10^{-7}$ | 26.37 ± 2.66 | 18.82 ± 1.50 | 0.607 ± 0.044 |

Example 3-2 (Evaluation of Bone Formation)

A human osteoblast (SAM-1, 20 PDL) was cultured in α-MEM containing 10% fetal bovine serum at 37° C. in 5% $CO_2$/95% air. After cells became confluent, the test compound at the given concentration was added in the presence of 2 mM α-glycerophosphate, and the cell culture was continued for 18 days. The cell layer was washed with physiological saline and, then, an alkaline phosphatase activity (ALP) was determined from the optical density (OD) at 415 nm. Thereafter, calcium (Ca) and phosphorus (P) were extracted with 5% aqueous perchloric acid, followed by a quantitative determination.

The results are shown in Table 3-2.

TABLE 3-2

| Compound | Concentration (H) | Ca (mg/dl) | Pi mg/dl | ALP (ABS 415 mm) |
|---|---|---|---|---|
| Control (no compound) | — | 0.32 ± 0.002 | 0.40 ± 0.050 | 0.061 ± 0.013 |
| Example 2-5 | $1 \times 10^{-8}$ | 0.32 ± 0.04 | 0.49 ± 0.09 | 0.080 ± 0.006 |
| | $1 \times 10^{-7}$ | 0.42 ± 0.06 | 0.62 ± 0.02 | 0.208 ± 0.021 |
| Example 1-9 | $1 \times 10^{-8}$ | 0.28 ± 0.04 | 0.48 ± 0.02 | 0.048 ± 0.003 |
| | $1 \times 10^{-7}$ | 0.28 ± 0.02 | 0.44 ± 0.02 | 0.052 ± 0.005 |
| Example 1-10 | $1 \times 10^{-8}$ | 0.34 ± 0.04 | 0.50 ± 0.11 | 0.049 ± 0.003 |
| | $1 \times 10^{-7}$ | 0.33 ± 0.03 | 0.50 ± 0.04 | 0.051 ± 0.001 |
| Known compound* | $1 \times 10^{-8}$ | 0.31 ± 0.06 | 0.38 ± 0.04 | 0.052 ± 0.003 |
| | $1 \times 10^{-7}$ | 0.27 ± 0.04 | 0.35 ± 0.02 | 0.041 ± 0.016 |

*1: See Table 3-1

We claim:

1. A lactone compound having the formula (I):

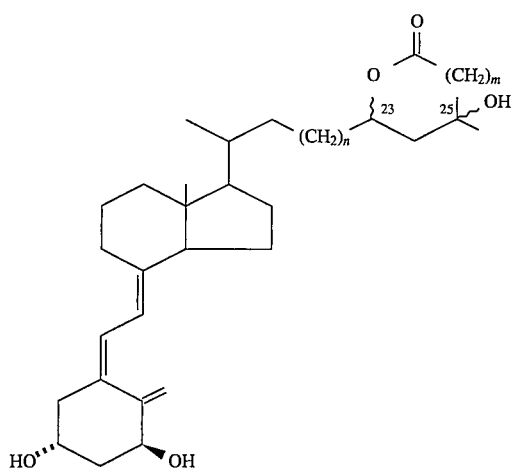

wherein n is zero or 1 and m is zero or 1, provided that both n and m are not zero at the same time, or a stereoisomer thereof at the 23- and/or 25-positions or any mixture thereof.

2. A 1α,25-dihydroxy-22-homomethylene-vitamin $D_3$-26, 23-lactone compound having the formula (II):

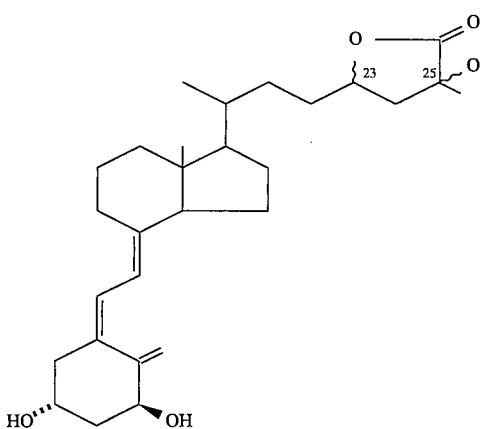

a stereoisomer thereof at 23- and/or 25-positions or any mixture thereof.

3. A lactone compound as claimed in claim 2, wherein an asymmetric center at C-23 is an (S) configuration and an asymmetric center at C-25 is an (R) configuration.

4. A lactone compound as claimed in claim 2, wherein an asymmetric center at C-23 is an (R) configuration and an asymmetric center at C-25 is an (R) configuration.

5. A 1α,25-dihydroxy-26-homomethylene-vitamin $D_3$-26, 23-lactone having the formula (III):

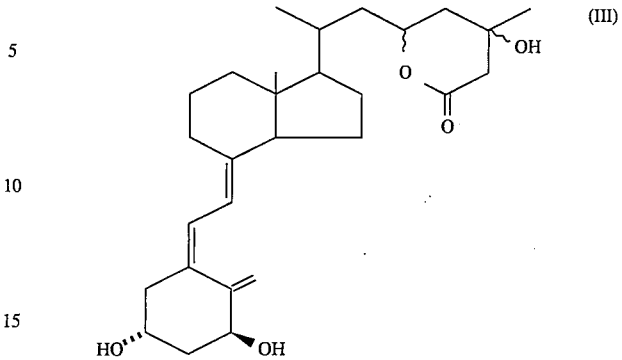

a stereoisomer thereof at the 23- and/or 25-positions of any mixture thereof.

6. A lactone compound as claimed in claim 5, wherein an asymmetric center at C-23 is an (S) configuration and an asymmetric center at C-25 is an (R) configuration.

7. A process for producing a lactone compound having the formula (I):

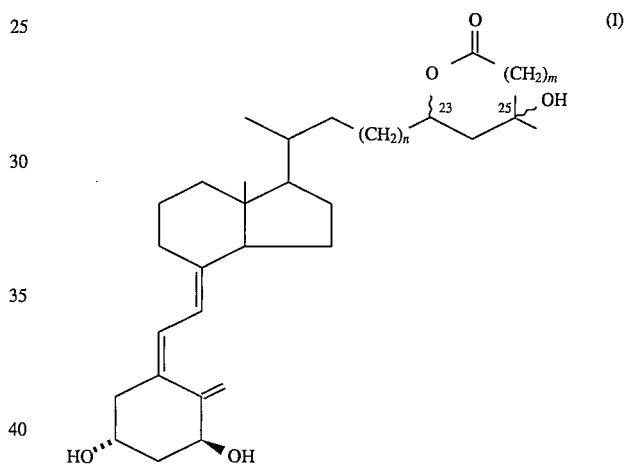

wherein n is zero or 1 and m is zero or 1, provided that both n and m are not zero at the same time, or a stereoisomer thereof at the 23- and/or 25-positions or any mixture thereof, or a 1α,25-dihydroxy-22-homomethylene-vitamin $D_3$-26, 23-lactone having an asymmetric center at C-23 of an (S) configuration and an asymmetric center at C-25 of an (R) configuration or having an asymmetric center at C-23 of an (R) configuration and an asymmetric center at C-25 of an (R) configuration, or 1α,25-dihydroxy-26-homomethylene-vitamin $D_3$-26,23-lactone comprising:

(i) halogenating (a) a lactone compound, which is a steroid compound having the formula (IV):

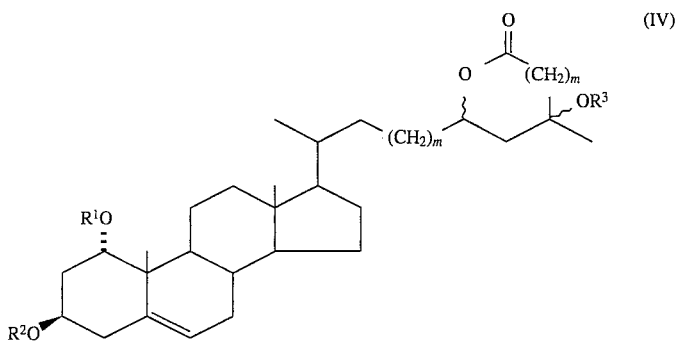

(IV)

wherein n is zero or 1 and m is zero or 1, provided that both n and m are not zero at the same time, $R^1$, $R^2$ and $R^3$ may be the same or different and represent a hydrogen atom, a tri($C_1$–$C_7$ hydrocarbon) silyl group, a $C_2$–$C_7$ acyl group or a group forming an acetal linkage together with an oxygen atom of a hydroxyl group, a stereoisomer thereof at the 23- and/or 25-positions or any mixture thereof, or (b) 1α,25-dihydroxy-22-homomethylene-cholest-5-ene-26,23-lactone, having an asymmetric center at C-23 of an (S) configuration and an asymmetric center at C-25 of an (R) configuration or having an asymmetric center at C-23 of an (R) configuration and an asymmetric center at C-25 of an (R) configuration or (c) 1α,25-dihydroxy-26-homomethylene-cholest-5-ene-26,23-lactone having an asymmetric center at C-23 of an (S) configuration and an asymmetric center at C-25 of an (R) configuration, followed by treating with a basic compound and, when the hydroxyl group is protected with a protecting group, removing the protecting group from the hydroxyl group, to thereby obtain (a) a lactone compound, which is a steroid compound having the formula (V):

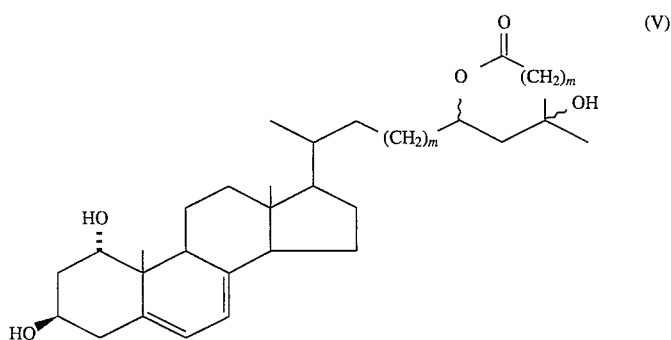

(V)

wherein n is zero or 1 and m is zero or 1, provided that both n and m are not zero at the same time, a stereoisomer thereof at the 23- and/or 25-positions or any mixture thereof or (b) 1α,25-dihydroxy-22-homomethylene-cholesta-5,7-diene-26,23-lactone, and (ii) subjecting the same to a photoisomerization reaction.

8. A process as claimed in claim 7, wherein the halogenation reaction is carried out with, as a halogenation agent, 1,3-dibromo-5,5-dimethylhydantoin.

9. A process as claimed in claim 7 or 8, wherein the basic compound is tetrabutyl ammonium fluoride.

10. An osteogenetic accelerator containing, as an active agent, the compound according to claim 1.

* * * * *